(12) United States Patent
Shekhter Zehavi et al.

(10) Patent No.: US 11,389,544 B2
(45) Date of Patent: Jul. 19, 2022

(54) FORMATION OF FUNCTIONALIZED CANCER TARGETING NANOPARTICLES BY SUPRAMOLECULAR CO-ASSEMBLY

(71) Applicants: RAMOT AT TEL-AVIV UNIVERSITY LTD., Tel Aviv (IL); TEL HASHOMER MEDICAL RESEARCH INFRASTRUCTURE AND SERVICES LTD., Ramat Gan (IL)

(72) Inventors: Talia Shekhter Zehavi, Petah-Tikva (IL); Ehud Gazit, Ramat-Hasharon (IL); Mor Herman-Oron, Ramat Efal Ramat Gan (IL); Genady Kostenich, Ramat Gan (IL); Arie Orenstein, Tel Aviv (IL)

(73) Assignees: RAMOT AT TEL-AVIV UNIVERSITY LTD., Tel Aviv (IL); TEL HASHOMER MEDICAL RESEARCH INFRASTRUCTURE AND SERVICES LTD., Ramat Gan (IL)

( * ) Notice: Subject to any disclaimer, the term of this patent is extended or adjusted under 35 U.S.C. 154(b) by 930 days.

(21) Appl. No.: 16/071,168

(22) PCT Filed: Jan. 19, 2017

(86) PCT No.: PCT/IL2017/050080
§ 371 (c)(1),
(2) Date: Jul. 19, 2018

(87) PCT Pub. No.: WO2017/125933
PCT Pub. Date: Jul. 27, 2017

(65) Prior Publication Data
US 2021/0170048 A1   Jun. 10, 2021

Related U.S. Application Data

(60) Provisional application No. 62/281,225, filed on Jan. 21, 2016.

(51) Int. Cl.
| | |
|---|---|
| *A61P 35/00* | (2006.01) |
| *A61K 47/69* | (2017.01) |
| *A61K 47/64* | (2017.01) |
| *A61K 47/60* | (2017.01) |
| *A61K 38/31* | (2006.01) |

(52) U.S. Cl.
CPC .......... *A61K 47/6929* (2017.08); *A61K 38/31* (2013.01); *A61K 47/60* (2017.08); *A61K 47/64* (2017.08); *A61P 35/00* (2018.01)

(58) Field of Classification Search
None
See application file for complete search history.

(56) References Cited

U.S. PATENT DOCUMENTS

| | | | |
|---|---|---|---|
| 6,123,916 A  * | 9/2000 | Krenning | A61P 35/00 424/1.69 |
| 6,355,613 B1 * | 3/2002 | Hornik | A61P 43/00 514/11.1 |

FOREIGN PATENT DOCUMENTS

| | | |
|---|---|---|
| WO | 2006027780 A2 | 3/2006 |
| WO | 2014132262 A1 | 9/2014 |

OTHER PUBLICATIONS

Adler-Abramovich and Gazit (2008) Controlled patterning of peptide nanotubes and nanospheres using inkjet printing technology. Journal of Peptide Science 14(2): 217-223.
Adler-Abramovich and Gazit (2014) The physical properties of supramolecular peptide assemblies: from building block association to technological applications. Chemical Society Reviews 43(20): 6881-6893.
Adler-Abramovich et al., (2009) Patterned arrays of ordered peptide nanostructures. Journal of nanoscience and nanotechnology 9(3): 1701-1708.
Adler-Abramovich et al., (2009) Self-assembled arrays of peptide nanotubes by vapour deposition. Nature nanotechnology 4(12): 849-854.
Barbieri et al., (2013) Peptide receptor targeting in cancer: the somatostatin paradigm. International journal of peptides 2013: 926295; 20 pages.
Castillo et al., (2014) Synthesis and characterization of covalent diphenylalanine nanotube-folic acid conjugates. Journal of nanoparticle research 16(7): 2525; 8 pages.
Falb et al., (2001) A bicyclic and hsst2 selective somatostatin analogue: design, synthesis, conformational analysis and binding. Bioorganic & medicinal chemistry 9(12): 3255-3264.
Fichman and Gazit (2014) Self-assembly of short peptides to form hydrogels: Design of building blocks, physical properties and technological applications. Acta biomaterialia 10(4): 1671-1682.
Frederix et al., (2015) Exploring the sequence space for (tri-) peptide self-assembly to design and discover new hydrogels. Nature chemistry 7(1): 30-37.
Gazal et al., (2001) Synthesis of novel protected Nα(ω-thioalkyl) amino acid building units and their incorporation in backbone cyclic disulfide and thioetheric bridged peptides. Chemical Biology & Drug Design 58(6): 527-539.
Gazit (2007) Self-assembled peptide nanostructures: the design of molecular building blocks and their technological utilization. Chemical Society Reviews 36(8): 1263-1269.

(Continued)

*Primary Examiner* — Elly-Gerald Stoica
(74) *Attorney, Agent, or Firm* — Browdy and Neimark, PLLC

(57) ABSTRACT

The present invention provides nanoparticle conjugates incorporating the self-assembling module diphenylalanine (FF) dipeptide into a bioactive moiety. The conjugate self-assembles to form distinct nanometric structures such as nanospheres. The present invention further provides nanoparticles formed by supramolecular co-assembly of the conjugates with a diphenylalanine (FF) dipeptide or analog thereof, to generate bioactive self-assembled nanostructures.

24 Claims, 20 Drawing Sheets

(56) References Cited

OTHER PUBLICATIONS

Gilon et al., (1998) A backbone-cyclic, receptor 5-selective somatostatin analogue: synthesis, bioactivity, and nuclear magnetic resonance conformational analysis. Journal of medicinal chemistry 41(6): 919-929.

Gour et al., (2012) Controlling morphology of peptide-based soft structures by covalent modifications. Journal of Peptide Science 18(6): 405-412.

Keskin and Yalcin (2013) A review of the use of somatostatin analogs in oncology. OncoTargets and therapy 6: 471-483.

Kostenich et al., (2005) Targeting small-cell lung cancer with novel fluorescent analogs of somatostatin. Lung Cancer 60(3): 319-328.

Levin et al., (2014) Ostwald's rule of stages governs structural transitions and morphology of dipeptide supramolecular polymers. Nature communications 5: 5219; 8 pages.

Mahler et al., (2006) Rigid, self-assembled hydrogel composed of a modified aromatic dipeptide. Advanced Materials 18(11): 1365-1370.

Orbach et al., (2009) Self-assembled Fmoc-peptides as a platform for the formation of nanostructures and hydrogels. Biomacromolecules 10(9): 2646-2651.

Reches and Gazit (2003) Casting metal nanowires within discrete self-assembled peptide nanotubes. Science 300 (5619): 625-627.

Reches and Gazit (2004) Formation of closed-cage nanostructures by self-assembly of aromatic dipeptides. Nano letters 4(4): 581-585.

Reches and Gazit (2005) Self-assembly of peptide nanotubes and amyloid-like structures by charged-termini-capped diphenylalanine peptide analogues. Israel journal of chemistry 45(3): 363-371.

Reches and Gazit (2007) Biological and chemical decoration of peptide nanostructures via biotin-avidin interactions. Journal of nanoscience and nanotechnology 7(7): 2239-2245.

Roth (1996) The silver anniversary of gold: 25 years of the colloidal gold marker system for immunocytochemistry and histochemistry. Histochemistry and cell biology 106(1): 1-8.

Sedman et al., (2013) Tuning the mechanical properties of self-assembled mixed-peptide tubes. Journal of microscopy 249(3): 165-172.

Shekhter Zahavi et al., (2017) Molecular Engineering of Somatostatin Analogue with Minimal Dipeptide Motif Induces the Formation of Functional Nanoparticles ChemNanoMat 3(1): 27-32 and supporting information.

Song et al., (2004) Synthesis of peptide-nanotube platinum-nanoparticle composites. Chemical Communications (9): 1044-1045.

Yan et al., (2010) Self-assembly and application of diphenylalanine-based nanostructures. Chemical Society Reviews 39(6): 1877-1890.

Yuran et al., (2012) Coassembly of aromatic dipeptides into biomolecular necklaces. ACS Nano 6(11): 9559-9566.

Zahavi et al., (2014) Engineered Hormone Analogs as Functionalized Self-Assembled Nanoparticles. Journal of Peptide Science 20(S1): S97-S98.

Zhang (2003) Fabrication of novel biomaterials through molecular self-assembly. Nature biotechnology 21(10): 1171-1178.

Zhou et al., (2009) Self-assembled peptide-based hydrogels as scaffolds for anchorage-dependent cells. Biomaterials 30(13): 2523-2530.

Li et al., (2013) The conjugation of nonsteroidal anti-inflammatory drugs (NSAID) to small peptides for generating multifunctional supramolecular nanofibers/hydrogels. Beilstein J.Org Chem 9: 908-917.

Wang et al., (2013) Kinetically controlled self-assembly of redox-active ferrocene-diphenylalanine: from nanospheres to nanofibers. Nanotechnology 24(46): 465603; 11 pages.

Zahavi et al., "Engineered hormone analogs as functionalized self-assembled nanoparticles". Presented at the 80th Annual Meeting of the Israel Chemical Society, Feb. 17-18, 2015, David Intercontinental Hotel, Tel-Aviv, Israel. Retrieved from the Internet: URL: https://bioforumconf.com/chemistry_abs/outofhtml/80th_meeting/engineeredhorm_Talia_Shekhter_Zahavi.html, on Mar. 25, 2019. Abstract, 1 page.

* cited by examiner

FORMATION OF FUNCTIONALIZED CANCER TARGETING NANOPARTICLES BY SUPRAMOLECULAR CO-ASSEMBLY

FIELD OF THE INVENTION

The present invention provides nanoparticle conjugates incorporating the self-assembling module diphenylalanine (FF) dipeptide into a bioactive moiety. The conjugate self-assembles to form distinct nanometric structures such as nanospheres. The present invention further provides nanoparticles formed by supramolecular co-assembly of the conjugates with a diphenylalanine (FF) dipeptide or analog thereof, to generate bioactive self-assembled nanostructures.

BACKGROUND OF THE INVENTION

Self-assembling peptides are valuable building blocks that can be rationally designed to organize into a variety of supramolecular nanostructures, such as tubes, fibrils, spheres, and other architectures. The nanostructures formed by short peptides may possess molecular recognition properties, great versatility, and could be easily modified both chemically and biologically to be used for medical applications due to their inherent biocompatibility and biodegradability.

The diphenylalanine peptide (FF) is considered as a key recognition module, as this small elementary unit and its derivatives readily self-assemble to form spherical, fibrillar and tubular nanostructures through π-stacking and additional non-covalent interactions.[1-12] Tert-butoxycarbonyl diphenylalanine (Boc-FF), a member of the FF dipeptide structural family, can also self-organize into various structures at the nano-scale. It was previously reported that Boc-FF has the ability to form nanospheres with metallic-like stiffness. FF derivatives undergo a phase transition process that displays a variety of structural phases, from spheres to tubes. A comprehensive screen of all 8,000 natural tripeptides revealed that all 13 tripeptides with the highest aggregation propensity contain a pair of neighboring aromatic amino acids and at least one phenylalanine residue, with six of the top aggregating tripeptides containing the FF motif.[13] Although the significance of FF and its propensity to form ordered nanostructures has been established for short peptides, its ability to direct the assembly of much larger full-length polypeptides has not been demonstrated.

Supramolecular co-assembly of different aromatic self-assembling building blocks allows the variation, complexity and functionality of the nanostructures with varied compositions, complexity and functionality which may possess physical and chemical properties that differ from structures obtained from single components. It has been previously shown that the FF peptide has the ability to co-assemble with its Boc-protected analog. Mixing FF and Boc-FF resulted in the formation of ordered dimorphic structures. Fmoc-amino acids and short peptides form rigid macroscopic nanostructures and hydrogels.[4] When two other aromatic short peptide derivatives, 9-fluorenylmethoxycarbonyl (Fmoc) modified peptide, Fmoc-FF, and Fmoc-RGD (arginine-glycine-aspartate), were dissolved together, a bioactive hydrogel was formed.[14] In addition, the FF peptide could co-assemble with another FF derivative to form mixed-peptide nanotubes.[15] These assemblies and co-assemblies have great potential in a wide range of nanotechnological and biotechnological applications.[9, 12, 16, 17]

FF peptides can be easily modified with biological and chemical moieties for various applications. For example, it was demonstrated that FF peptide nanotubes were functionalized via biotin-avidin interactions, and by covalent conjugation of folic acid.[18, 19]

The use of nano-systems as a platform for target-specific delivery of chemotherapeutic agents has a great potential in cancer therapy. Delivery systems of therapeutics and diagnostics have emerged from passive delivery, which mainly relies on selective accumulation of particles in tumor tissues exploiting the enhanced permeability and retention (EPR) effect. This phenomenon, combined with active targeted delivery, of which targeting capacity is dependent on specific targeting agents, improves drug efficacy and diagnostic signal and reduces harmful nonspecific side effects. Tumor targeting moieties, therapeutic agents and imaging probes can be multiplexed into a single nanocarrier for controlled tumor delivery.

Somatostatin is a cyclopeptide hormone consisting of 14 or 28 amino acids (SRIF-14 and SRIF-28). It is an important regulator of endocrine and exocrine secretion, affecting the release of various key hormones (e.g., growth hormone, glucagon, insulin). Somatostatin acts on multiple cell targets via a family of five receptors (somatostatin receptors; SSTR1-5). In addition to their expression in normal tissues, SSTRs are often overexpressed in various tumors, such as neuroendocrine tumors, breast cancer, lymphomas, lung cancer and thyroid carcinomas. While SSTRs are important therapeutic targets, somatostatin has a short half-life, thus employing the peptide as a therapeutic agent was found to be challenging. As a result, more stable synthetic analogs have been developed and can be used in clinical applications.[20, 21] One of those is the stable and tumor-selective somatostatin analog PTR 3207 which can be used for clinical applications.

There exists an unmet need for efficient biocompatible systems, capable of targeted delivery of active moieties for therapeutic, imaging and diagnostic purposes.

SUMMARY OF THE INVENTION

The present invention provides nanoparticle conjugates incorporating the self-assembling module diphenylalanine (FF) dipeptide into a bioactive moiety. The conjugates self-assemble to form distinct nanometric structures such as nanospheres. The present invention further provides nanoparticles formed by supramolecular co-assembly of the conjugates with a diphenylalanine (FF) dipeptide or analog thereof, to generate bioactive self-assembled nanostructures.

Self-assembled peptides have immense potential in diverse nanotechnological applications. Due to their biocompatibility, chemical diversity, and modular structure, these peptides could serve as building blocks for various nanomedical purposes. The extension of the self-organization into a supramolecular co-assembly process allows the introduction of additional properties into nanoparticles. As a representative embodiment, the present invention provides for the first time a platform in which a diphenylalanine (FF), a minimal self-assembling module was incorporated with a peptide-based cancer-specific moiety, a somatostatin analog. The conjugation of the highly effective very short aromatic peptide motif to the bioactive sequence induced the self-assembly of the chimeric peptide into ordered nanostructures. Furthermore, in another embodiment, supramolecular co-assembly of the engineered hormone together with a tert-butoxycarbonyl (Boc) modified nano-sphere forming diphenylalanine analog allowed the formation of bioactive homogenous spherical nanostructures. The formation of the well-organized nanospheres was characterized by transmission electron microscopy, atomic force microscopy and dynamic light scattering. The loading ability of the closed-caged engineered nanostructures was established and the binding capacity of the hybrid assemblies to cancer cells was verified. These findings present a new strategy for functionalization to engineer self-assembling peptides for drug delivery applications that also could be used for the modification of other targeting analogs as well as for the design and synthesis of more complex co-assembled nanoparticles.

The present invention is based on a multifunctional approach which offers a diagnostic and therapeutic potential for the treatment of a variety of diseases such as cancer by combining peptide targeted delivery and nanotechnology. The present invention is based on combining peptide targeting and self-assembly properties alongside the utilization of co-assembly for the formation of multi-functional bioactive nanostructures. In one embodiment as described herein, tumor selective somatostatin analog (PTR 3207) was conjugated to FF motif to form FF-PTR peptide. The FF motif was chosen due to its high propensity to self-assemble into ordered nanometric structures to induce the self-organization of the FF hybrid molecule and co-organization with FF-based building blocks. As a representative spacer, a polyethylene glycol (PEG) derived linker (using, e.g., a linker derived from Fmoc-8-amino-3,6-dioxaoctanoic acid) may be used as a reagent to couple these two components to form either amine free conjugate (FIG. 1a) or its Fmoc-protected derivative (FIG. 1b). In accordance with this embodiment, the moiety linking the two components is represented by the structure (abbreviated herein "-(PEG)$_2$-"):

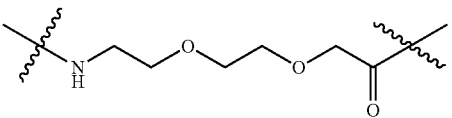 [SMILES: *NCCOCCOCC(*)=O]

As contemplated herein, the conjugation of FF motif to a bioactive moiety, for example, a short hormone analog, promotes the hybrid to self-organize into ordered nanostructures. These hybrid assemblies may target the tumor both passively, due to its size and structure, as well as actively due to somatostatin analog binding. Furthermore, in another embodiment, supramolecular co-assemblies were designed that include both FF-modified hybrids and Boc-FF as building block units. Without wishing to be bound to any particular theory or mechanism of action, it is contemplated that co-assembly with Boc-FF peptide may prevent the steric hindrance between the targeting moieties (FIG. 2a) and would function as a spacer to achieve better binding to cancer cells (FIG. 2b).

The principles of the present invention are not limited to the aforementioned embodiments directed to somatostatin analogs, and can be applied to a broad range of active agents and FF dipeptide combinations, for a variety of biological applications, e.g., drug delivery, therapeutic and diagnostic applications, as described herein.

Thus, in one embodiment, the present invention relates to a nanoparticle comprising a self-assembled conjugate of a diphenylalanine (FF) dipeptide or analog thereof, covalently bound, directly or through a linker, to a bioactive moiety selected from the group consisting of a therapeutically active agent, a biological substance, a cosmetic agent, a cell targeting moiety, a labelling moiety, a radioactive moiety, an imaging agent and a diagnostic agent.

In some embodiments, the diphenylalanine (FF) dipeptide or analog thereof is diphenylalanine (FF) or a protected diphenylalanine (FF). In some embodiments, the diphenylalanine (FF) comprises a protecting group on the terminal amino group ("amino-protected diphenylalanine"). Examples of amino-protected diphenylalanine (FF) include 9-fluorenylmethoxycarbonyl diphenylalanine (Fmoc-FF), t-butoxycarbonyl-diphenylalanine (Boc-FF), benzyloxycarbonyl (Cbz) diphenylalanine (Cbz-FF), acyl-diphenylalanine (Ac-FF), and silyl phenylalanine (silyl-FF). Each possibility represents a separate embodiment of the present invention.

According to the principles of the present invention, the diphenylalanine (FF) dipeptide or analog thereof is conjugated to the active moiety directly or through a linker, with each possibility representing a separate embodiment of the present invention. In some currently preferred embodiments, the linker is based on or derived from polyethylene glycol (PEG) (e.g., a PEG$_2$ linker described above). In other embodiments, the linker is selected from the group consisting of: a linear or branched C1-C20 alkylene, C2-C20 alkenylene, C2-C20 alkynylene and arylene moiety, each of which optionally incorporates one or more heteroatoms (e.g., O, N, S) in the chain, and which is optionally substituted at either or both ends with a group selected from the group consisting of —NH—, —C(=O)—, —O—, —S—, —C(=O)—O—, —O—C(=O)—O—, —C(=O)—NH—, —NH—C(=O)—NH—, NH—C(=O)—O—, —S(=O)—, —S(=O)—O—, —PO(=O)—O—, and any combination thereof. Each possibility represents a separate embodiment of the present invention.

A broad range of bioactive moieties can be used to form the conjugates of the present invention. In some representative embodiments, the active moiety may be selected from the group consisting of hormones, drugs, peptides (including cyclic peptides), polypeptides, proteins, enzymes, growth factors, nucleic acids, microorganisms, fluorescence compounds or moieties, phosphorescence compounds or moieties, radioactive compounds or moieties, inorganic nanoparticles useful for biological applications and any combination thereof. Each possibility represents a separate embodiment of the present invention.

In one particular embodiment, the active moiety is an anti-cancer drug, for example a hormone or hormone analog. In a currently preferred embodiment, the hormone analog is a somatostatin analog.

In some embodiments, the nanoparticles have a diameter between about 50 nm and about 250 nm.

The nanoparticles of the present invention may self-assemble into a variety of structures, including but not limited to nanospheres, nanotubes, nanofibrils and ribbon-like nanostructures. Each possibility represents a separate embodiment of the present invention.

In another aspect, the present invention relates to nanostructures formed by supramolecular co-assembly of the self-assembled conjugates described above, and a diphenylalanine (FF) dipeptide or analog thereof. The diphenylalanine (FF) dipeptide is preferably co-assembled with the conjugate through non-covalent interactions. In some embodiments, the diphenylalanine (FF) dipeptide or analog thereof is diphenylalanine (FF) or a protected diphenylalanine (FF) selected from the group consisting of an amino-protected diphenylalanine (FF) dipeptide, a carboxy-protected diphenylalanine (FF) dipeptide (i.e., diphenylalanine comprising a protecting group on the terminal carboxy group), an amino-protected, carboxy-protected diphenylalanine (FF) dipeptide (i.e., diphenylalanine comprising a protecting group on both the terminal amino and terminal carboxy groups), and combinations thereof. Each possibility represents a separate embodiment of the present invention.

In particular embodiments, the amino-protected diphenylalanine (FF) dipeptide is selected from the group consisting of t-butoxycarbonyl-diphenylalanine (Boc-FF), 9-fluorenylmethoxycarbonyl diphenylalanine (Fmoc-FF), benzyloxycarbonyl (Cbz) diphenylalanine (Cbz-FF) acyl-diphenylalanine (Ac-FF) and silyl phenylalanine (silyl-FF). Each possibility represents a separate embodiment of the present invention.

In some embodiments, the ratio between the conjugate and the diphenylalanine (FF) dipeptide is about 1 to about 10, preferably about 1 to about 4. Each possibility represents a separate embodiment of the present invention.

In some embodiments, the co-assembled nanoparticles have a diameter between about 50 nm to about 250 nm, as measured by dynamic light scattering (DLS).

The co-assembled nanoparticles may self-assemble into a variety of structures, such as nanospheres, nanotubes, nanofibrils and ribbon-like nanostructures. Each possibility represents a separate embodiment of the present invention.

In additional embodiments, the present invention further relates to pharmaceutical compositions comprising the nanoparticle as described herein, and a pharmaceutically or cosmetically acceptable carrier.

In other embodiments, the present invention further relates to a nanoparticle as described herein, for use in the preparation of pharmaceutical composition.

In other embodiments, the present invention further relates to a nanoparticle as described herein, for use for the delivery of drugs.

In other embodiments, the present invention further relates to a nanoparticle as described herein, for use as a targeting agent for delivery of anti-cancer drugs to a target tumor.

In other embodiments the present invention further relates to a nanoparticle as described herein, for use as an imaging agent.

In other embodiments, the present invention relates to the use of diphenylalanine (FF) or an analog thereof, for assembling a peptide, polypeptide or protein into a nanometric structure so as to enhance the half-life of said peptide, polypeptide or protein in a biological sample. In some embodiments, the diphenylalanine (FF) dipeptide or analog thereof is Fmoc-FF or Boc-FF, which is used to enhance the half-life of a protein in the body of a subject.

In some specific embodiments, the present invention relates to a somatostatin or a somatostatin analog covalently conjugated to FF dipeptide or FF dipeptide analog. In one exemplary embodiment, the nanoparticle is represented by the structure:

FF-(PEG)$_2$-PTR wherein PTR is somatostatin or analog thereof, FF is diphenylalanine or analog thereof, and (PEG)$_2$ is a linker derived from polyethylene glycol as defined above. In one specific embodiment, the nanoparticle is represented by the structure depicted in FIG. 1a.

In other embodiments, the nanoparticle is represented by the structure

Fmoc-FF-(PEG)$_2$-PTR wherein PTR is somatostatin or analog thereof, Fmoc-FF is 9-fluorenylmethoxycarbonyl diphenylalanine, and (PEG)$_2$ is a linker derived from polyethylene glycol as defined above. In one specific embodiment, the nanoparticle is represented by the structure depicted in FIG. 1b.

In other embodiments, the present invention relates to a somatostatin analog covalently conjugated to FF dipeptide or FF dipeptide analog as described above, for use as a delivery system of chemotherapy to a target tumor.

In other embodiments, the present invention relates to a somatostatin analog covalently conjugated to FF dipeptide or FF dipeptide analog as described above, for use as a delivery system of chemotherapy in pancreatic cancer.

In other embodiments, the present invention relates to a somatostatin analog covalently conjugated to FF dipeptide or FF dipeptide analog, co-assembled with FF dipeptide or FF dipeptide analog. In some embodiments, the conjugate is represented by the structure:

Fmoc-FF-(PEG)$_2$-PTR:Boc-FF (1:4)

wherein PTR is somatostatin or analog thereof, Fmoc-FF is 9-fluorenylmethoxycarbonyl diphenylalanine, Boc-FF is t-butoxycarbonyl diphenylalanine, and (PEG)$_2$ is a linker derived from polyethylene glycol as defined above, and wherein Fmoc-FF-(PEG)$_2$-PTR is represented by the structures as depicted in FIG. 1b.

In other embodiments, the present invention relates to a somatostatin analog covalently conjugated to FF dipeptide or FF dipeptide analog, co-assembled with FF dipeptide or FF dipeptide analog as described above, for use as a delivery system of chemotherapy to a target tumor.

In other embodiments, the present invention relates to a somatostatin analog covalently conjugated to FF dipeptide or FF dipeptide analog, co-assembled with FF or FF analog as described above, for use as a delivery system of chemotherapy in pancreatic cancer.

In additional embodiments, the present invention relates to a method of preparing the nanoparticle described herein, the method comprising the step of covalently conjugating a bioactive moiety, directly or through a linker, to diphenylalanine (FF) dipeptide or analog thereof, under conditions sufficient to form a self-assembled conjugate.

In other embodiments, the present invention relates to a method of preparing supramolecular co-assembled nanoparticles as described herein, the method comprising the steps of:

(a) covalently conjugating said active moiety, directly or through a linker, to diphenylalanine (FF) dipeptide or analog thereof, under conditions sufficient to form a self-assembled conjugate; and (b) contacting the product of step (a) with diphenylalanine (FF) dipeptide or analog thereof, under conditions sufficient to form a supramolecular structure, wherein the diphenylalanine (FF) or analog thereof is co-assembled with the conjugate of step (a) through non-covalent interactions.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The Fmoc protected precursor of a. (c) A control analog in which the PTR is conjugated to a $PEG_2$ linker with no assembly motif.

Figure 2A:
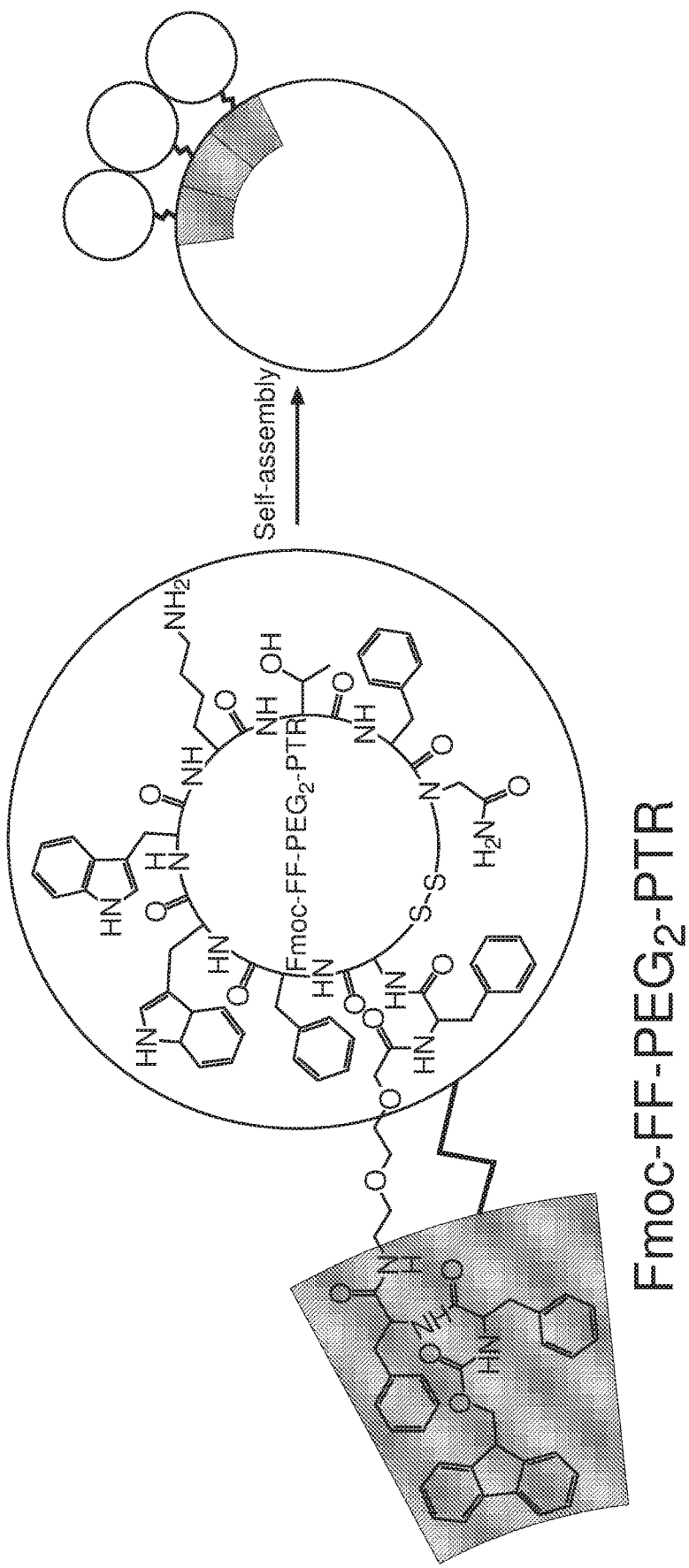
Figure 2B:
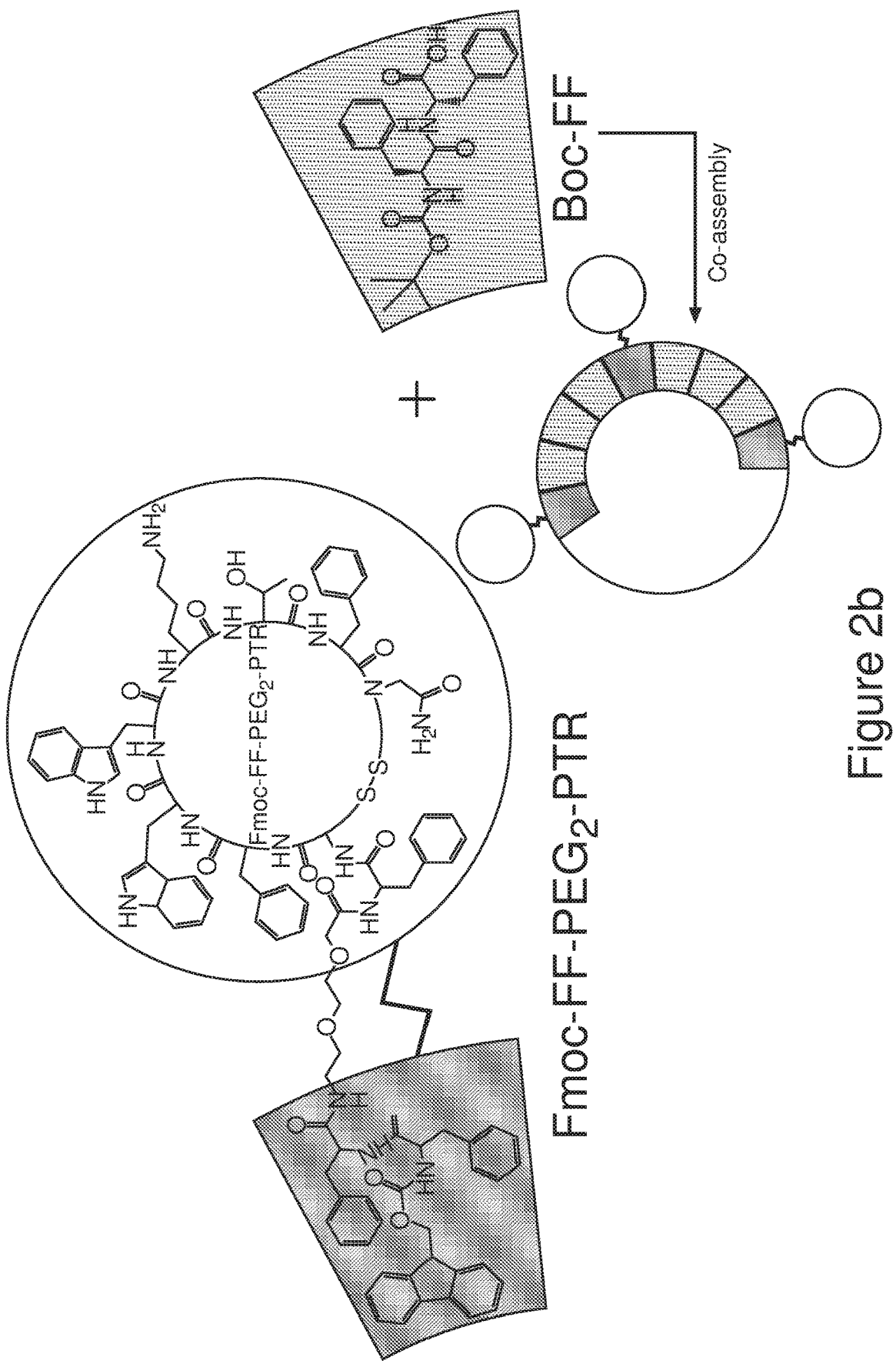

FIG. 2: Proposed schematic model of Fmoc-FF-$PEG_2$-PTR assemblies. Spherical nanostructures could be formed by the assembly of the modified hormone analog (FIG. 2a). The addition of the Boc-FF was envisioned to result in nano-spherical co-assemblies in which spacing by the Boc-FF building blocks allows the prevention of steric hindrance in binding of the nano-assemblies to target cells (FIG. 2b).

Figure 3:
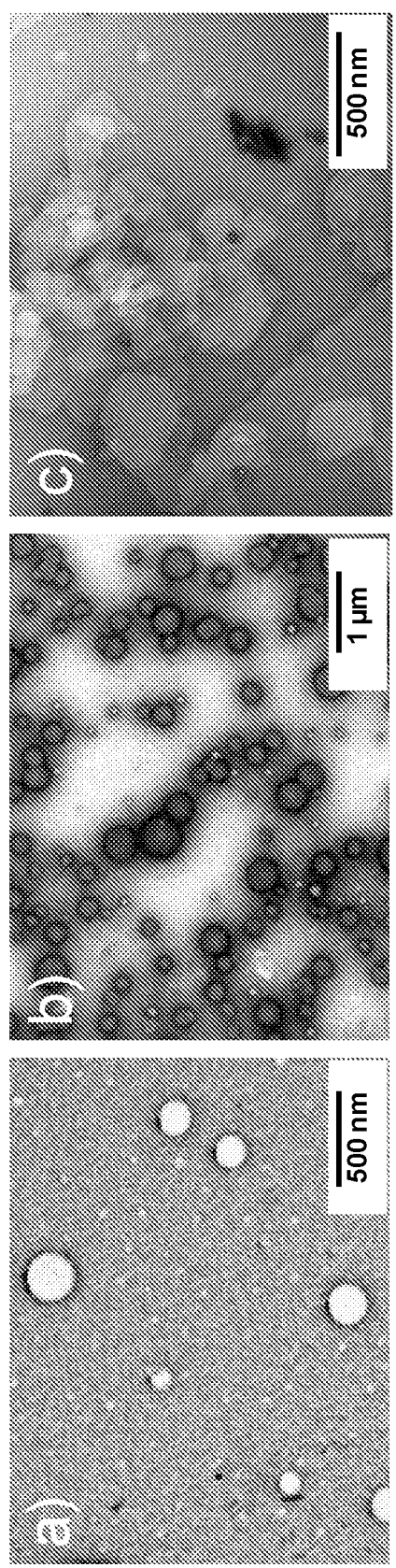

FIG. 3: TEM images of 0.6 mM PTR conjugates in 10% HFIP/$H_2O$. (a) $NH_2$-FF-$PEG_2$-PTR, (b) Fmoc-FF-$PEG_2$-PTR, (c) $NH_2$-$PEG_2$-PTR.

Figure 4:
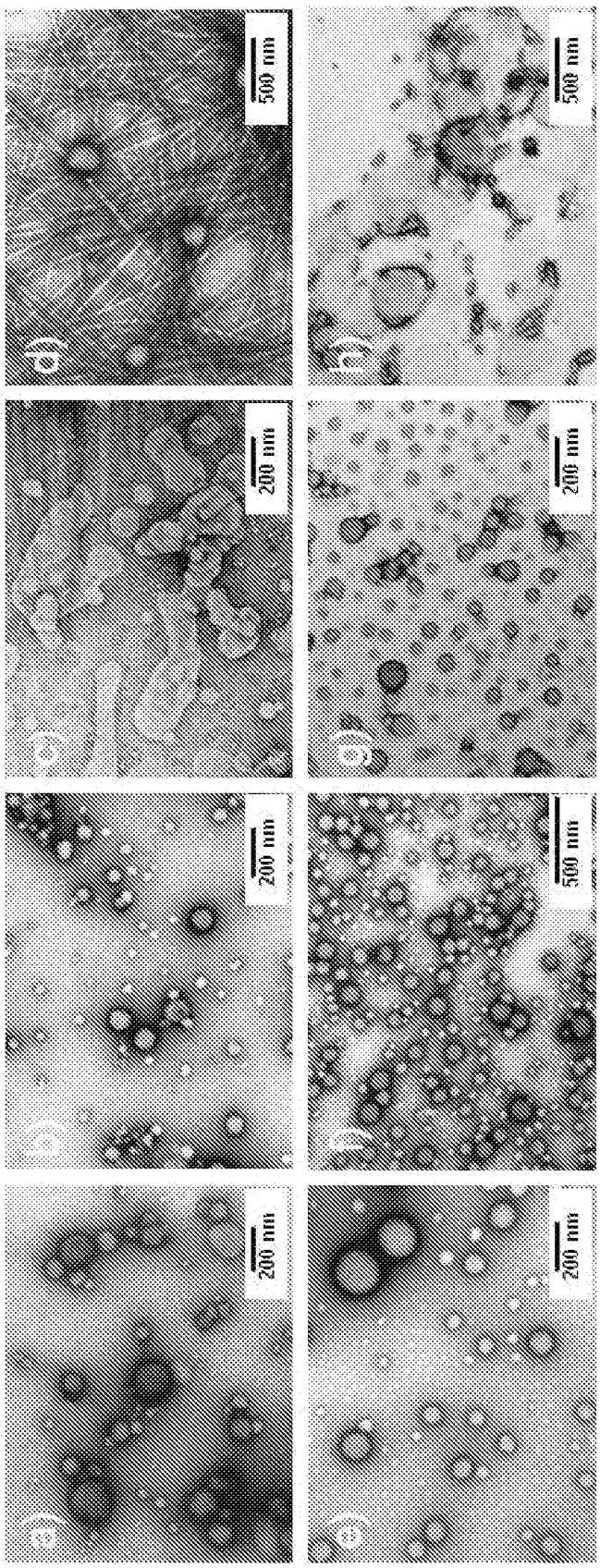

FIG. 4: Ultrastructure of the peptides assemblies and co-assemblies in 10% ethanol/$H_2O$. TEM images of 0.12-3 mM peptides. (a) $NH_2$-FF-$PEG_2$-PTR, (b) Fmoc-FF-$PEG_2$-PTR, (c) $NH_2$-$PEG_2$-PTR, (d) Boc-FF, (e) Fmoc-FF-$PEG_2$-PTR and Boc-FF mixture 1:2, (f) (1:4), (g) 1:10, (h) $NH_2$-$PEG_2$-PTR:Boc-FF (1:4).

Figure 5A:
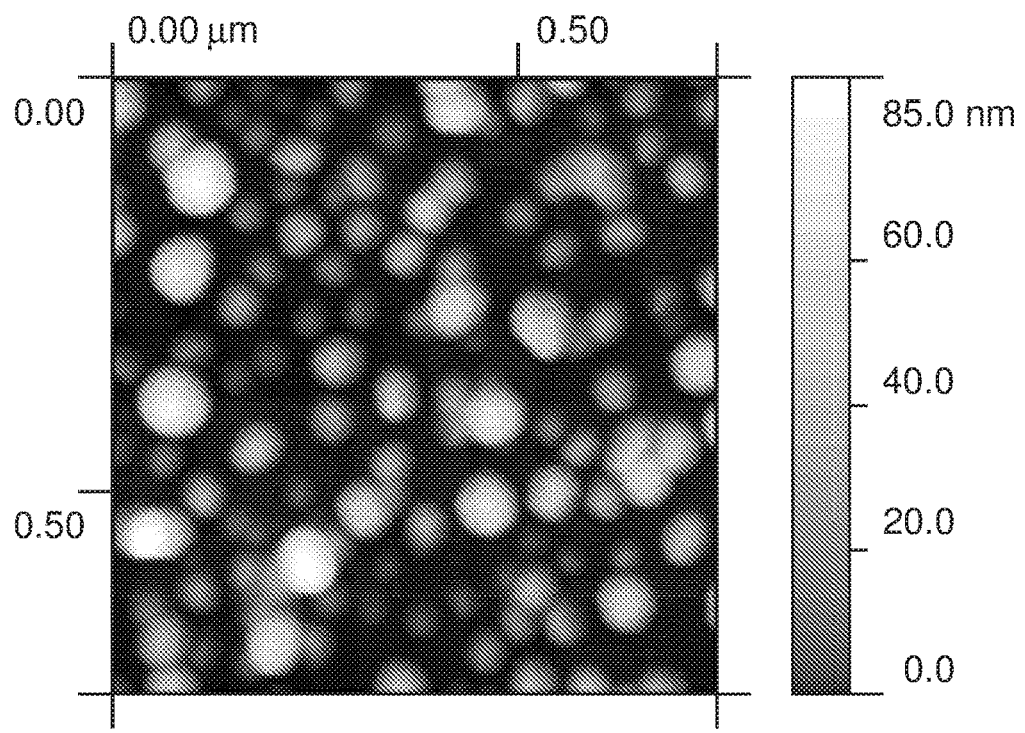
Figure 5B:
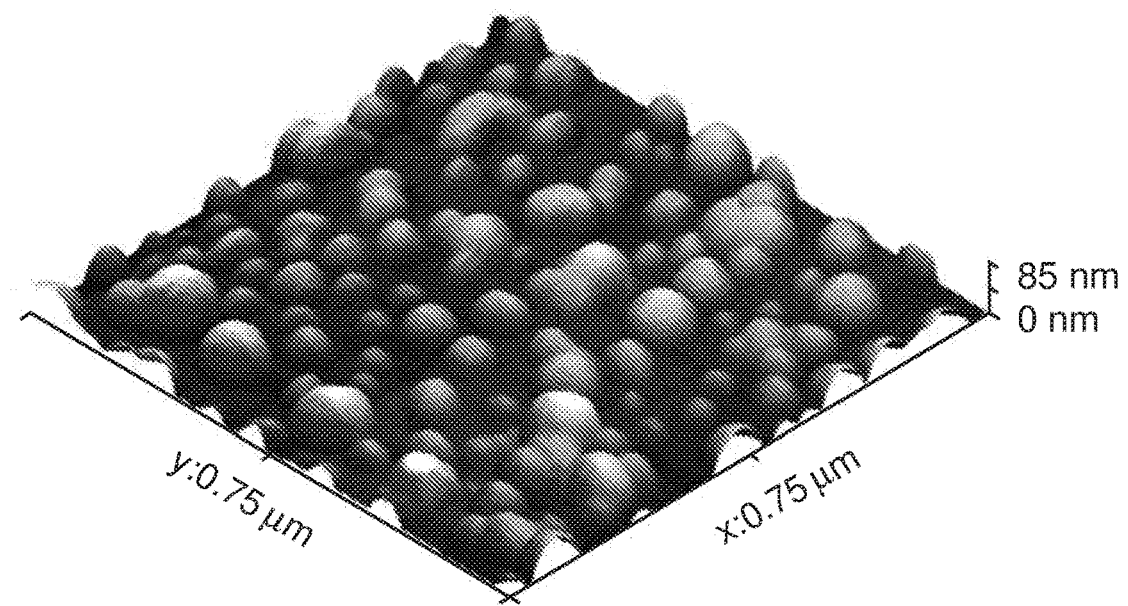
Figure 5:
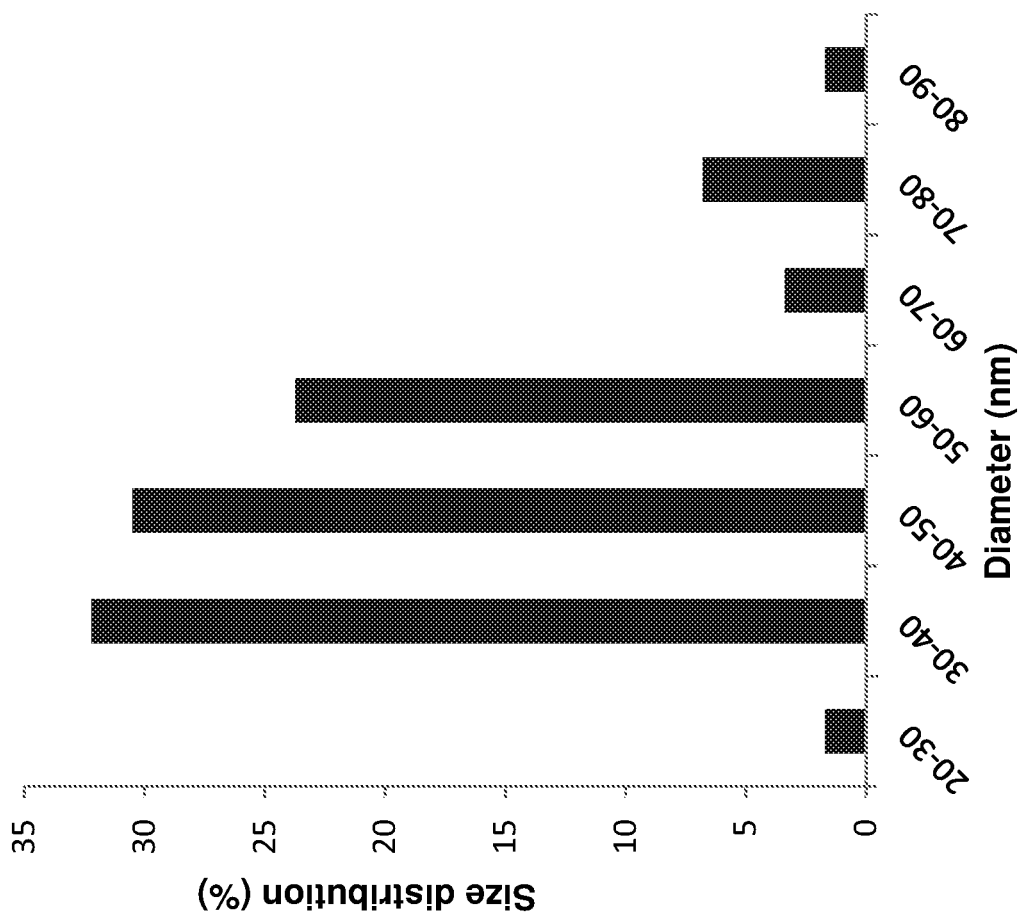

FIG. 5: AFM images of Fmoc-FF-$PEG_2$-PTR:Boc-FF (1:4) spheres. (a) Topography images of nanospheres deposited on freshly cleaved mica (scan area 0.75×0.75 μm). (b) Three-dimensional topography representation. (c) Size distribution of 60 spheres.

Figure 6:
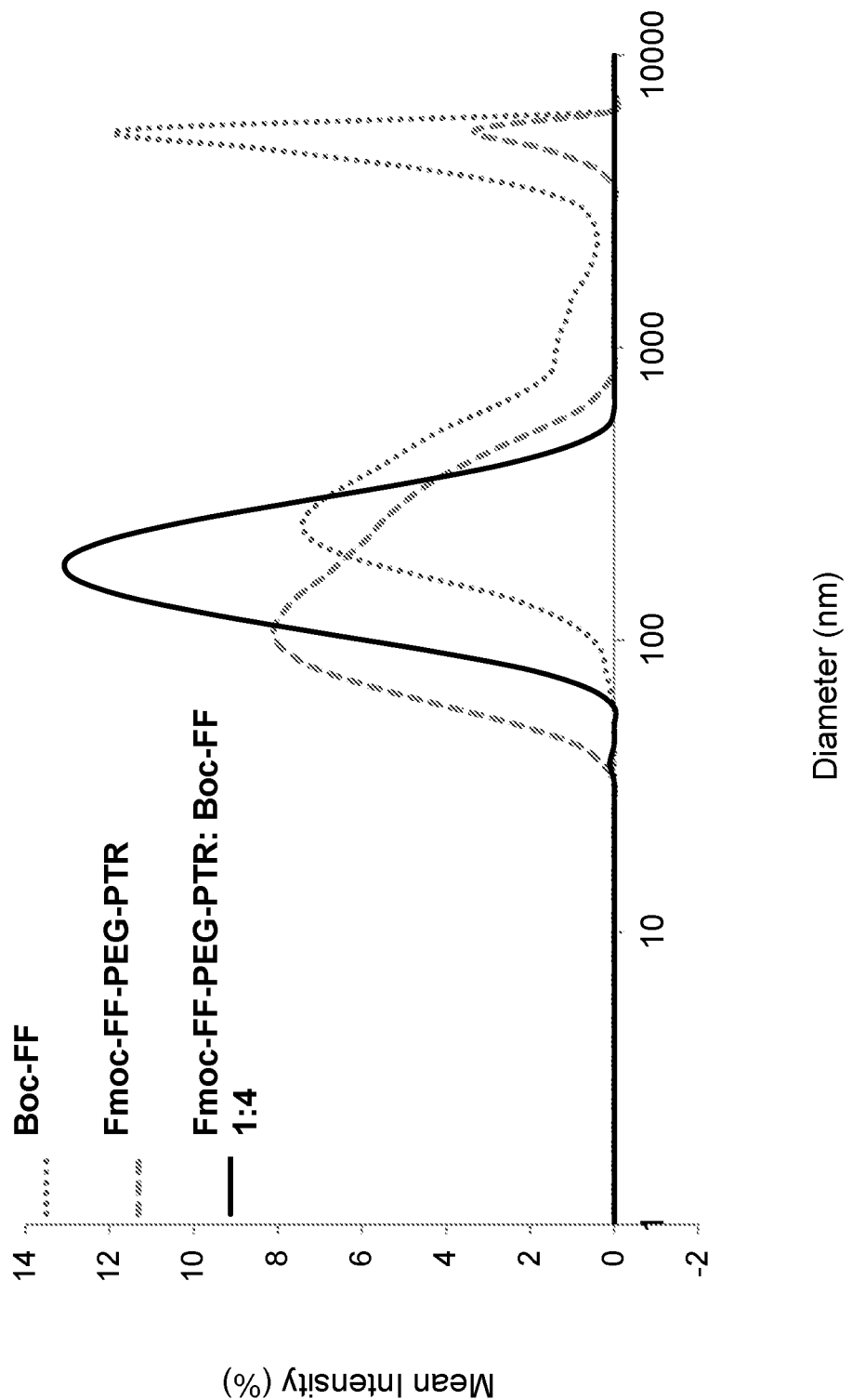

FIG. 6: Size distribution of peptide assemblies and co-assemblies. DLS analysis of Boc-FF (***), Fmoc-FF-$PEG_2$-PTR (---) and Fmoc-FF-$PEG_2$-PTR:Boc-FF (—).

Figure 7:
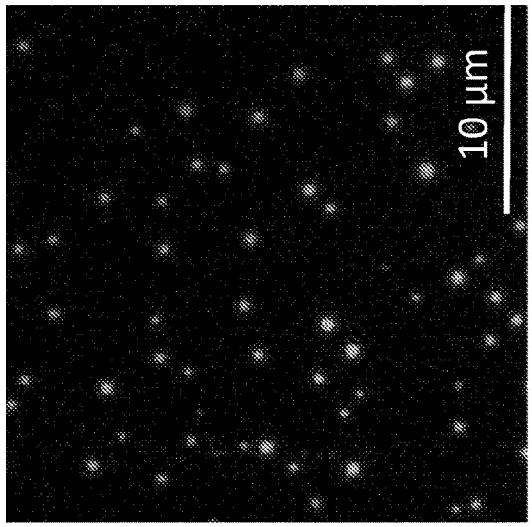
Figure 7:
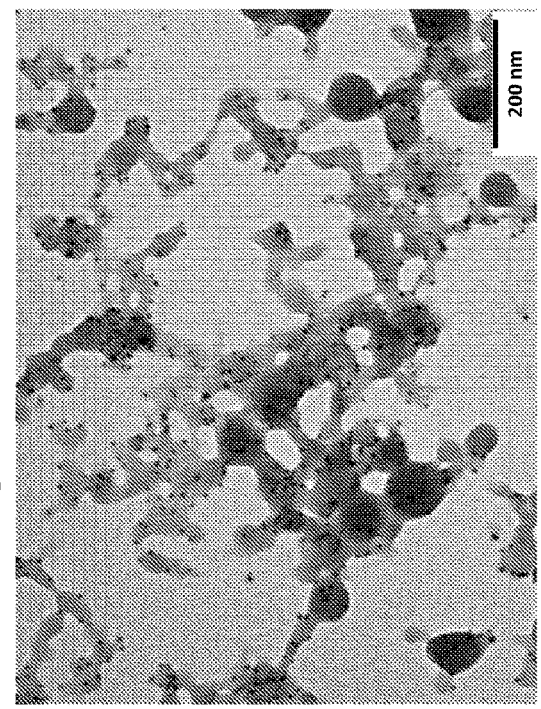
Figure 7:
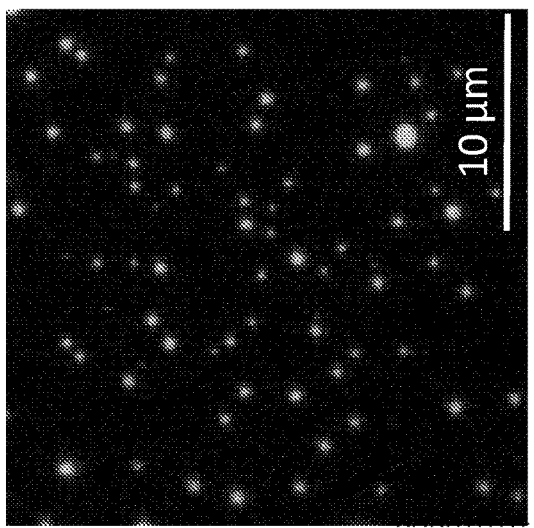
Figure 7:
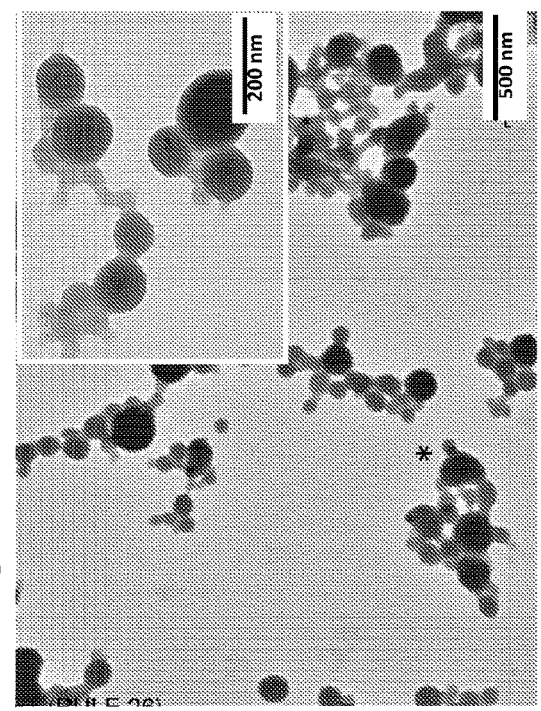

FIG. 7: Encapsulation of carboxyfluorescein and AuNPs into the peptides nanospheres. STED microscopy image of self-assembled and co-assembled nanospheres encapsulated with carboxyfluorescein: (a) 0.3 mM Fmoc-FF-$PEG_2$-PTR, (b) 0.3 mM Fmoc-FF-$PEG_2$-PTR:Boc-FF (1:4) spheres. TEM images of nanospheres encapsulated with 50% AuNPs (5 nm), (c) 0.3 mM Fmoc-FF-$PEG_2$-PTR, (d) 0.3 mM Fmoc-FF-$PEG_2$-PTR:Boc-FF (1:4) spheres.

Figure 8:
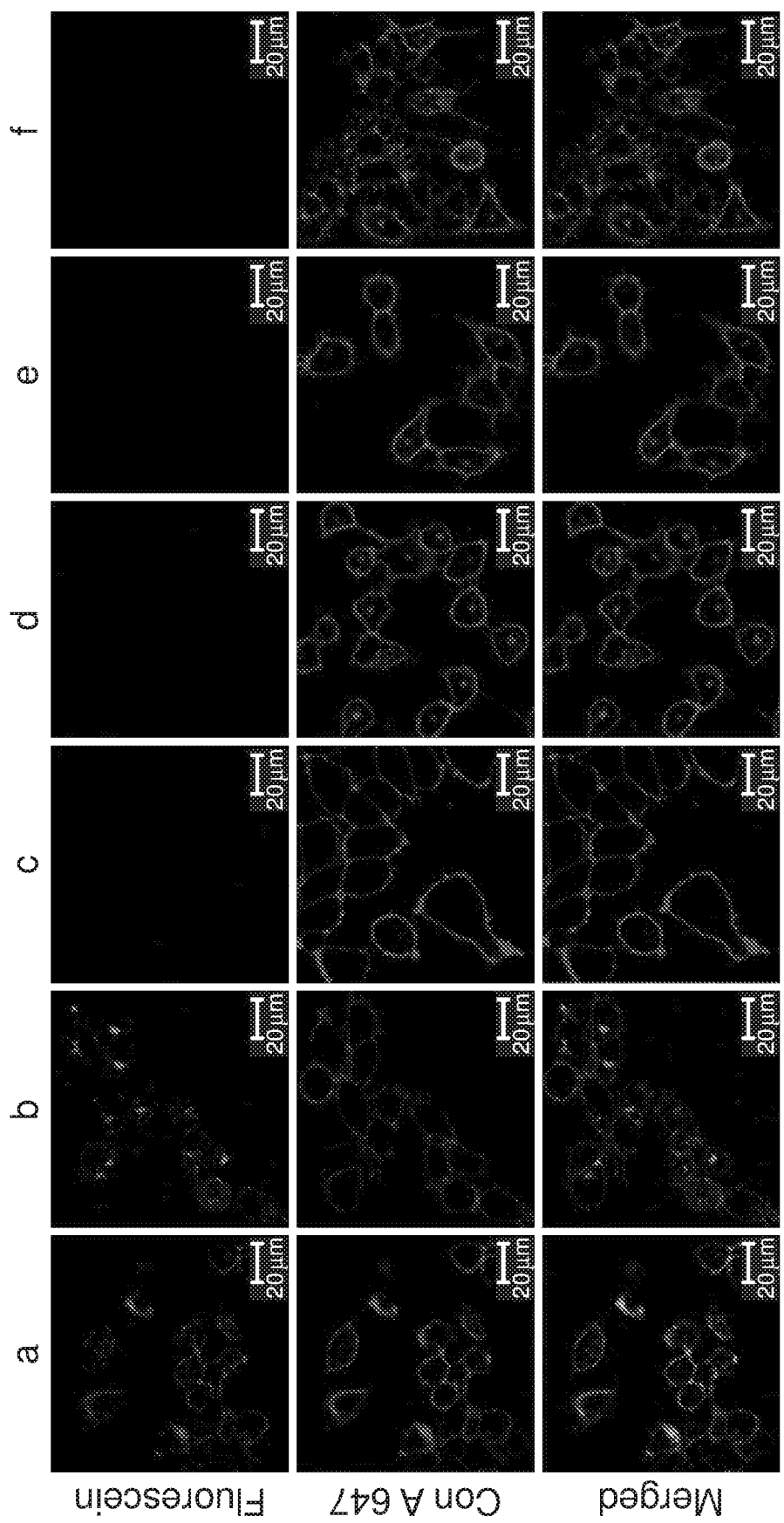

FIG. 8: Uptake of Fmoc-FF-$PEG_2$-PTR and Fmoc-FF-$PEG_2$-PTR BocFF (1:4) spheres to Panc-1 cancer cells. Confocal microscopy of Panc-1 cancer cells after 2 h incubation treated with Con A 647 (1 μg/ml) for 15 minutes: (a) 30 μM Fmoc-FF-$PEG_2$-PTR:Boc-FF (1:4) spheres encapsulated with 1.5 μM carboxyfluorescein, (b) 30 μM PTR-3207-FITC, (c) 30 μM Fmoc-FF-$PEG_2$-PTR spheres encapsulated with 1.5 μM carboxyfluorescein, (d) 7.5 μM BocFF with 1.5 μM carboxyfluorescein, (e) 1.5 μM carboxyfluorescein, (f) 1% ethanol.

Figure 9A:
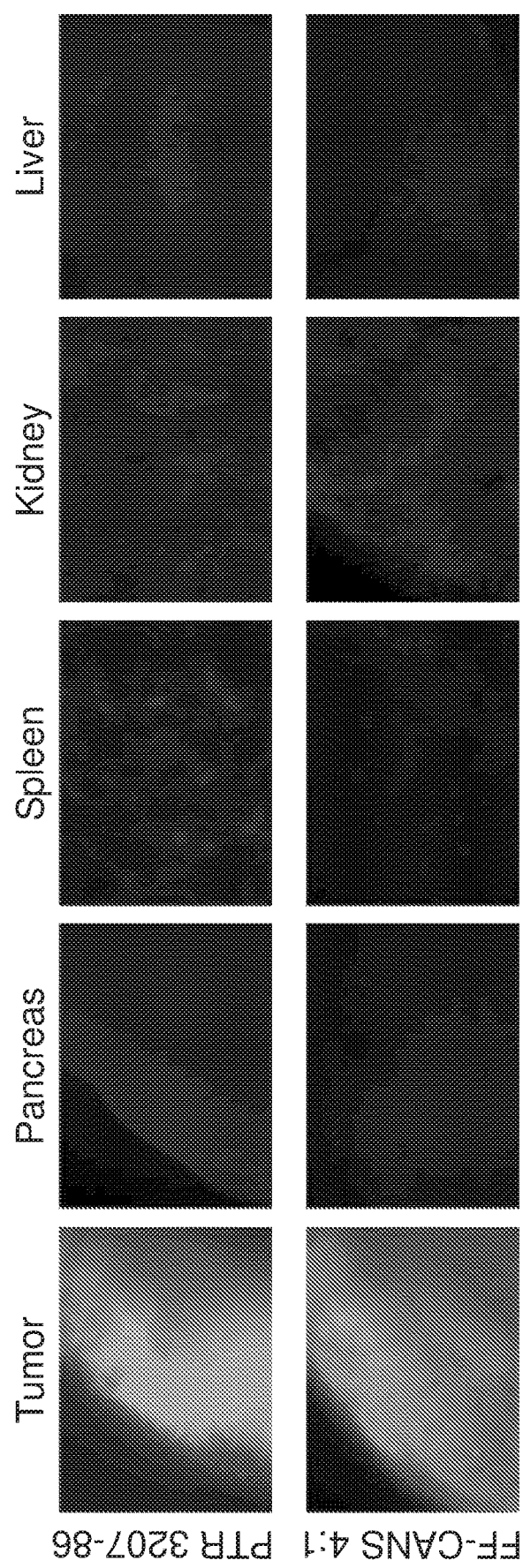
Figure 9:
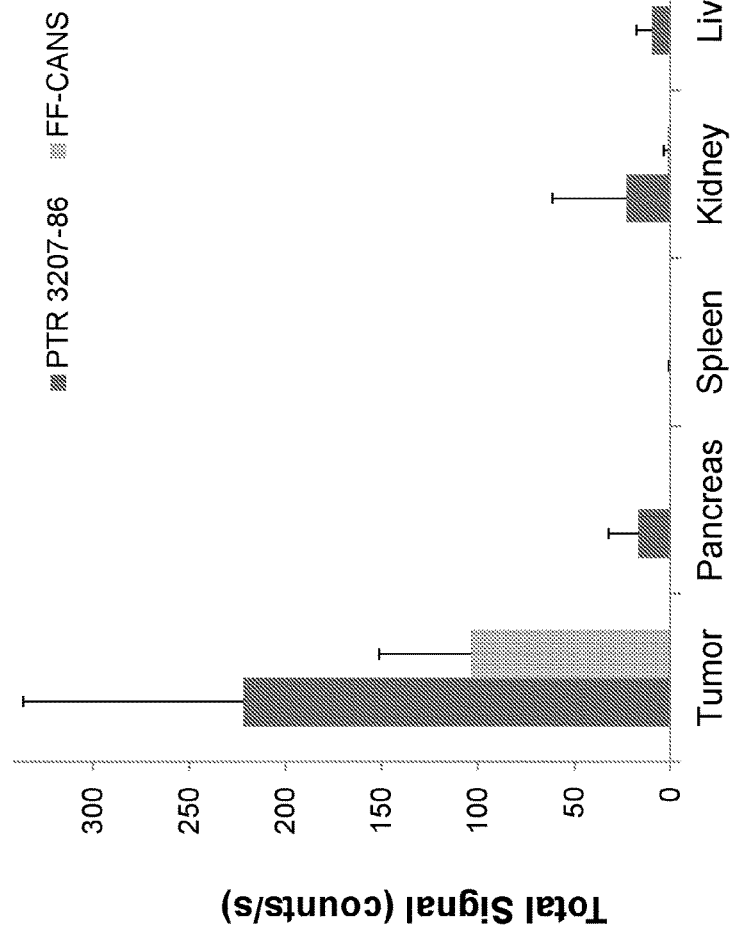
Figure 9:
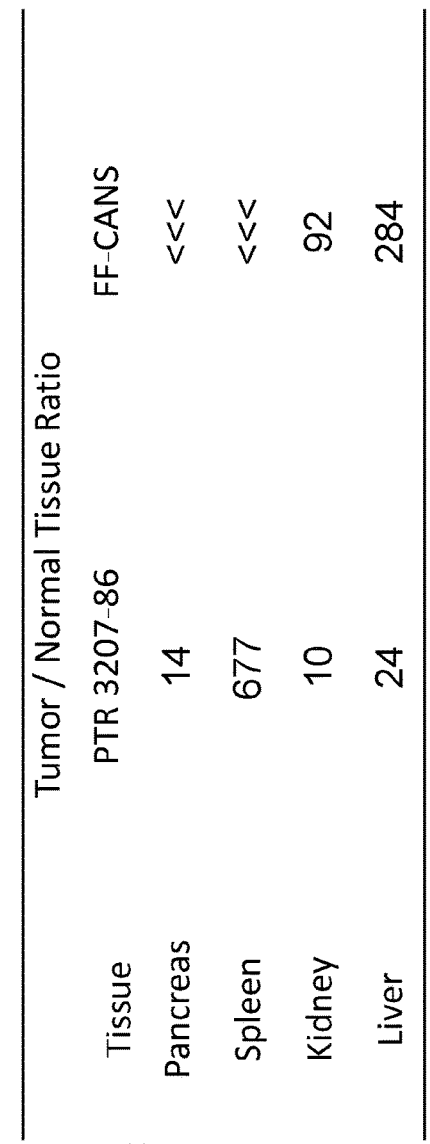

FIG. 9: Comparative biodistribution of Fmoc-FF-$PEG_2$-PTR BocFF (1:4) spheres compared to PTR 3207-86, somatostatin analog. Panc-1 xenografts were injected i.v. via the tail vein with 15 mg/Kg of PTR 3207-86 (300 μL) or with 15 mg/Kg FF-Fmoc-FF-$PEG_2$-PTR:BocFF (1:4) spheres (100 μL) encapsulated with carboxyfluorescein. The tumor and the organs were resected 24 hrs post injection. a) Fluorescent images of the organs, 200 ms exposure, ×40 magnification. b) Quantitative measurements of fluorescence intensities. Images were acquired using a CRI Maestro Imaging system ($\lambda ex$=455 nm, $\lambda em$=515 nm) and analyzed following auto-fluorescence. c) Calculated values of tumor to normal tissue ratios.

Figure 10A:
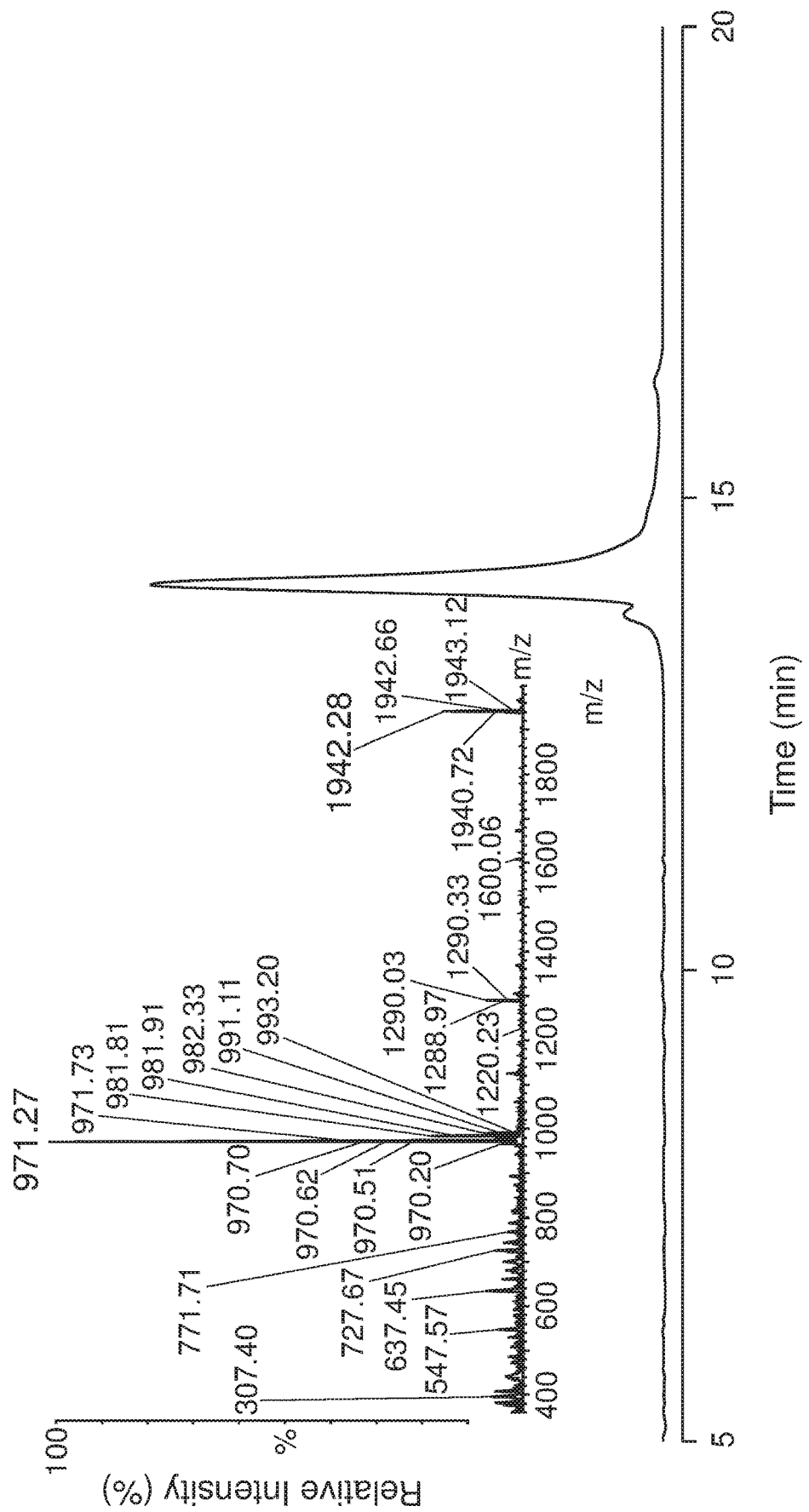
Figure 10B:
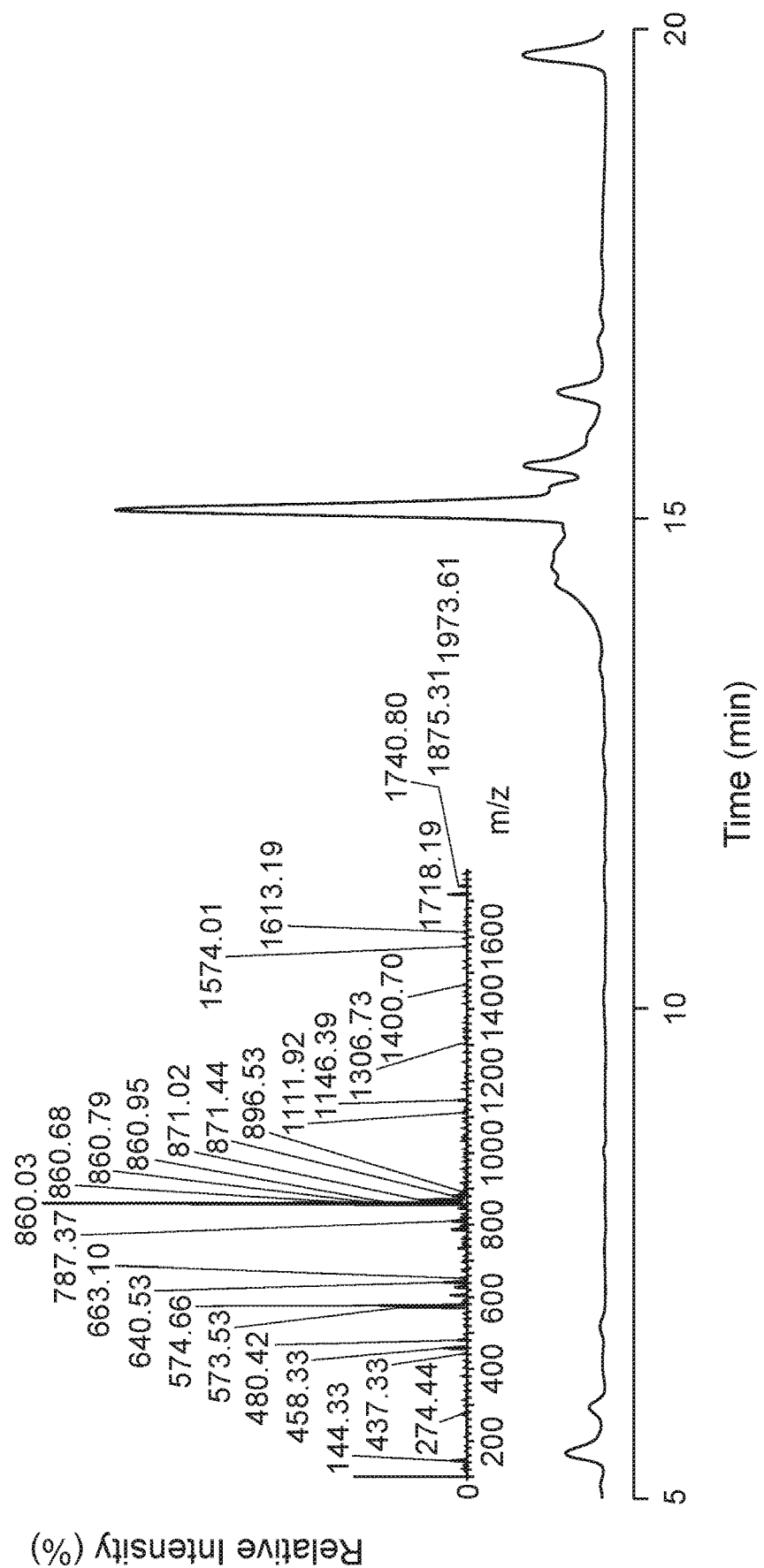
Figure 10C:
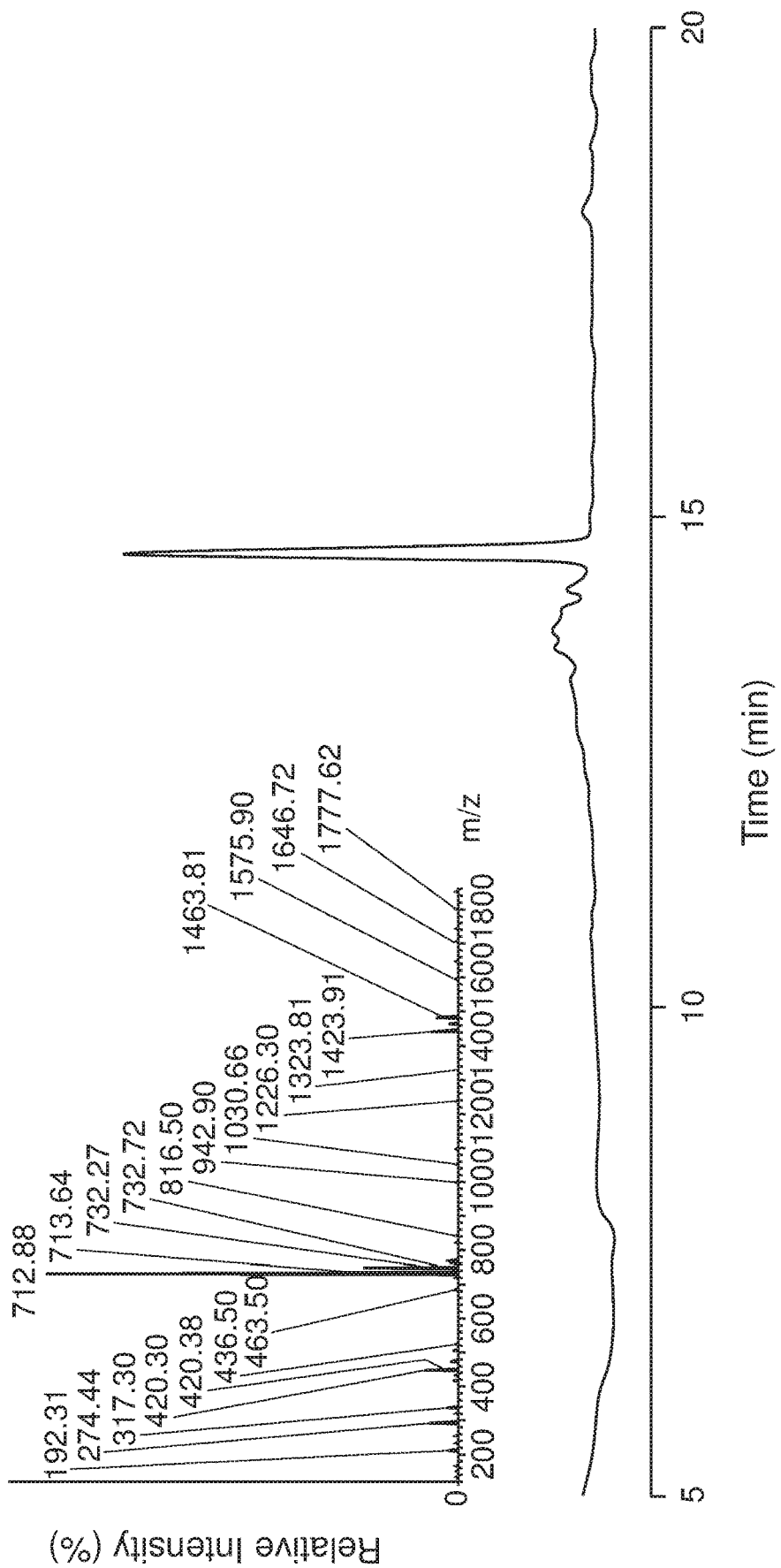

FIG. 10: Analytical RP-HPLC chromatograms and mass spectra of PTR conjugates. (a) Fmoc-FF-$PEG_2$-PTR. Gradient is 40-100% B (acetonitrile, 0.1% TFA) over 15 min Mass spec inset confirms the expected mass of 1941 Da. (b) $NH_2$-FF-$PEG_2$-PTR. Gradient is 30-70% B over 15 min. Mass spec inset confirms the expected mass of 1717 Da. (c) $NH_2$-$PEG_2$-PTR. Gradient is 20-70% B over 15 min. Mass spec inset confirms the expected mass of 1423 Da. HPLC flow rate 1 mL/min, wavelength 214 nm.

Figure 11:
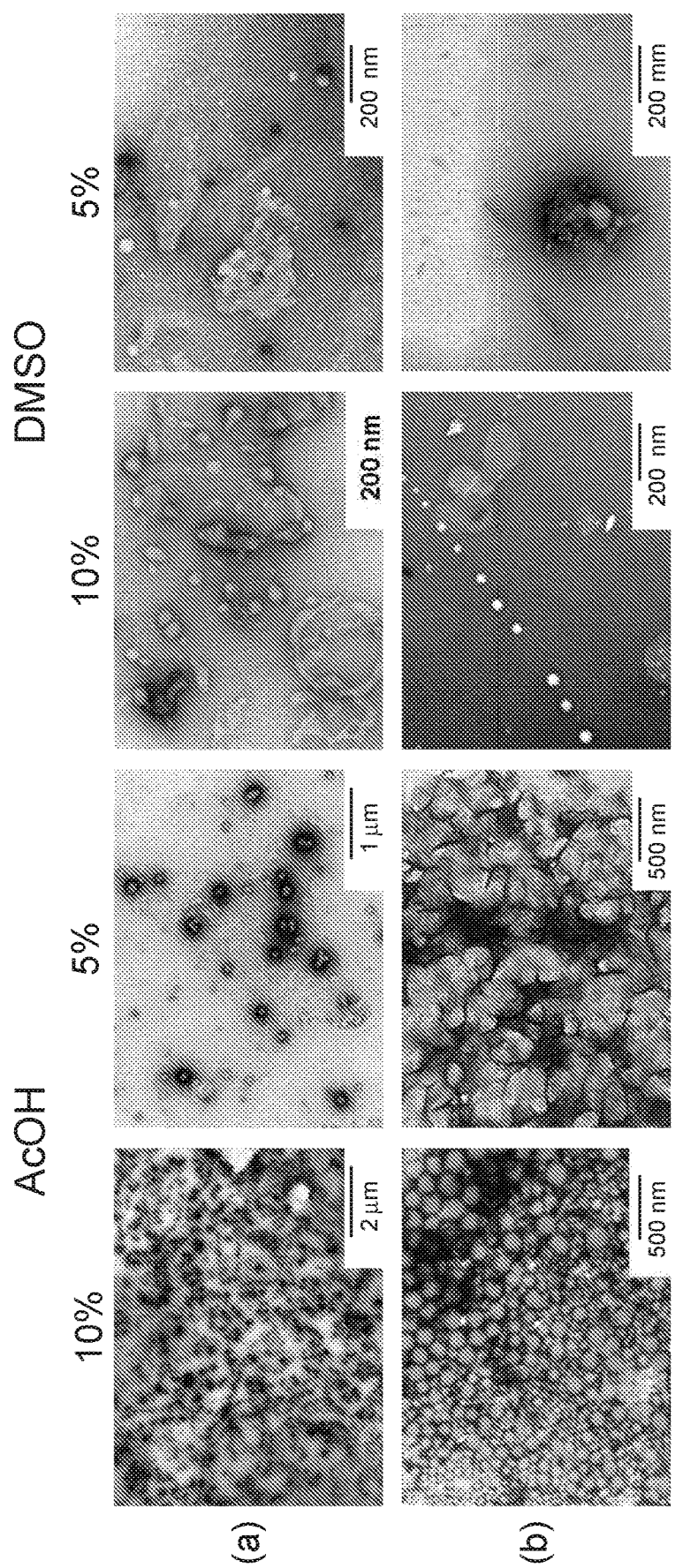

FIG. 11: TEM images of PTR-FF-conjugates dissolved in different 10% and 5% of acetic acid (AcOH)/ultra-pure water (UPW) or DMSO/UPW, peptide concentrations: 0.6 mM-0.3 mM. (a) $NH_2$-FF-$PEG_2$-PTR, (b) Fmoc-FF-$PEG_2$-PTR, (c) $NH_2$-$PEG_2$-PTR.

Figure 12:
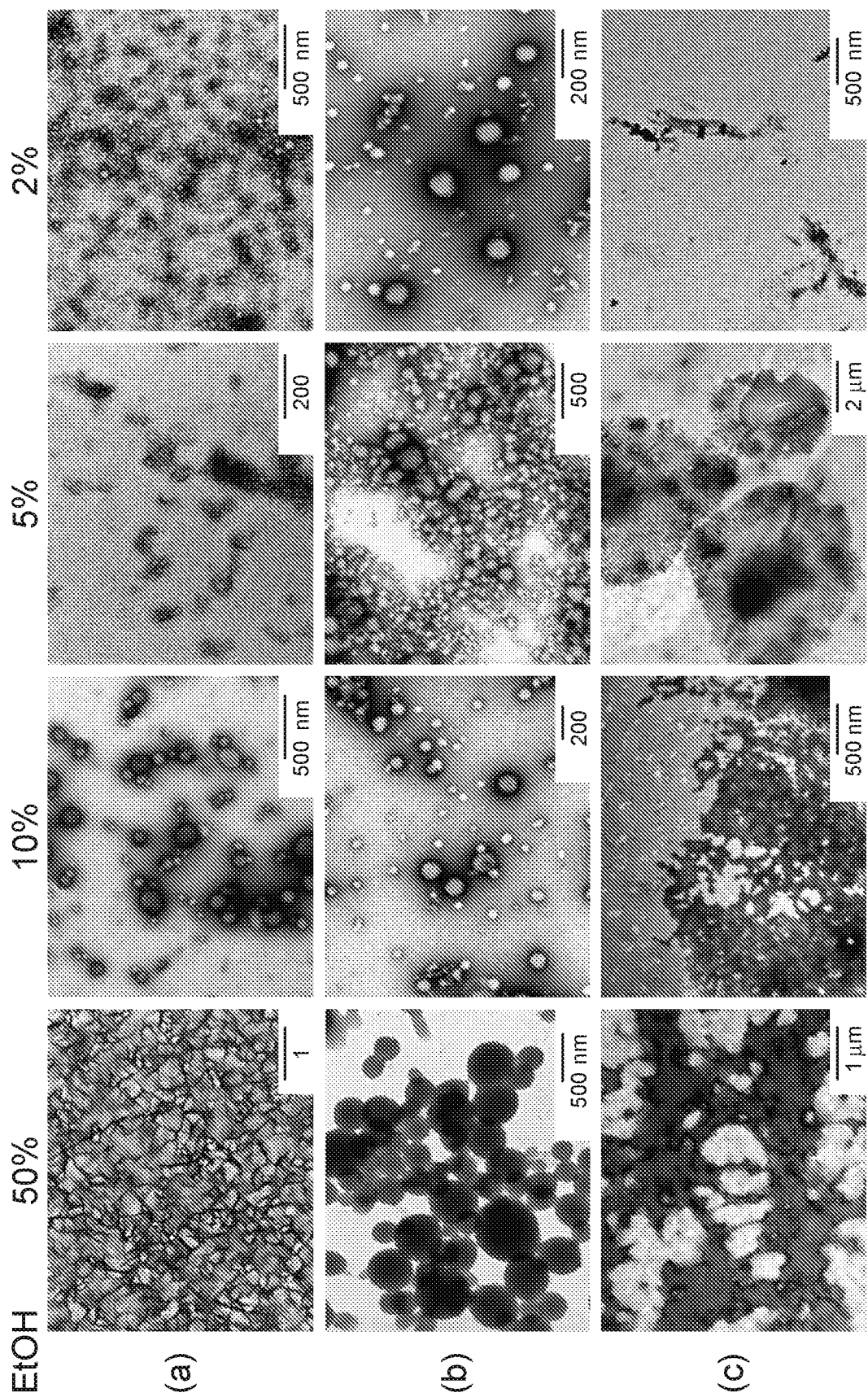

FIG. 12: TEM images of PTR-FF-conjugates dissolved in different percentages of ethanol/UPW, concentrations rang 3 mM-0.12 mM: (a) $NH_2$-FF-$PEG_2$-PTR, (b) Fmoc-FF-$PEG_2$-PTR, (c) $NH_2$-$PEG_2$-PTR.

Figure 13:
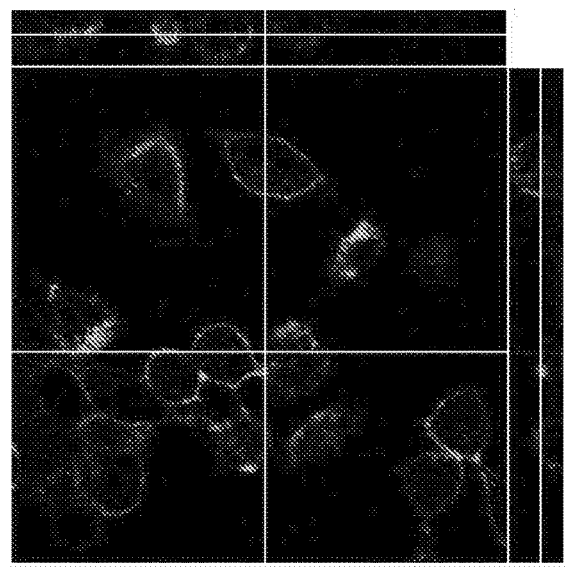

FIG. 13: Confocal microscopy cross-section image of Panc-1 cells incubated for 2 h with 30 μM Fmoc-FF-$PEG_2$-PTR BocFF (1:4) spheres encapsulated with 1.5 μM carboxyfluorescein and treated with Con A 647 (1 μg/ml) for 15 minutes.

Figures 14A, 14B:
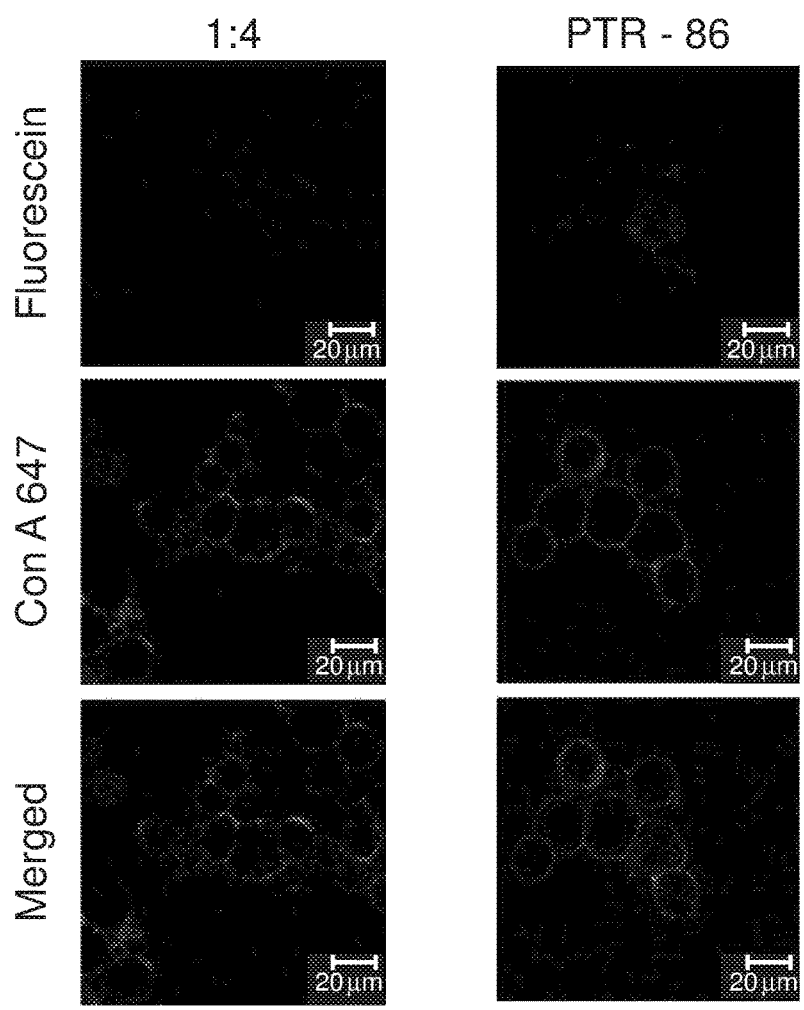

FIG. 14: Uptake of Fmoc-FF-$PEG_2$-PTR:BocFF (1:4) spheres to HEK-293T cells. Confocal microscopy of HEK-293T cells after 2 h incubation treated with Con A 647 (1 μg/ml) for 15 minutes: (a) 30 μM Fmoc-FF-$PEG_2$-PTR:Boc-FF (1:4) spheres encapsulated with 1.5 μM carboxyfluorescein, (b) 30 μM PTR-3207-FITC.

DETAILED DESCRIPTION OF THE PRESENT INVENTION

The present invention provides nanoparticle conjugates incorporating the self-assembling module diphenylalanine (FF) dipeptide into a bioactive moiety. The conjugates self-assemble to form distinct nanometric structures such as nanospheres. The present invention further provides nanoparticles formed by supramolecular co-assembly of the conjugates with a diphenylalanine (FF) dipeptide or analog thereof, to generate bioactive self-assembled nanostructures.

Definitions:

The term "peptide" as used herein refers to a plurality of amino acids (at least two), and encompasses native peptides (including degradation products, synthetically synthesized peptides or recombinant peptides) and peptidomimetics (typically, synthetically synthesized peptides), as well as peptoids and semipeptoids which are peptide analogs. The term "peptide" also encompasses a cyclic peptide, as exemplified herein by somatostatin or somatostatin analogs. The term "dipeptide" as used herein refers to a peptidic chain of two amino acids.

As used herein, the term "nanoparticle" or "nanostructure" refers to a physical structure, which in at least one dimension has a size ranging from about 1 nm to less than about 1,000 nm, for example about 10 nm or about 20 nm or about 50 nm to about 100 nm or about 200 nm or about 500 or less than about 1,000 nm, preferably about 20 nm to about 500 nm. In some embodiments, the self-assembled nanostructure according to the present invention has diameter between about 20 nm and about 500 nm. Nanostructures comprising a biological or chemical moiety (e.g., somatostatin-Fmoc FF nanostructures) typically have diameters ranging from about 50 nm to about 250 nm. In some embodiments, the nanoparticles have a diameter between about 50 nm and about 200 nm. Nanostructures comprising co-assembled supramolecuar structures (e.g., somatostatin-Fmoc FF nanostructures co-assembled with Boc-FF) typically have diameters ranging from about 20 nm to about 250 nm as measured, e.g., by dynamic light scattering (DLS).

As used herein the terms "tubular nanostructure" or spherical nanostructure", also referred to as "nanotubes" or "nanospheres", refer, respectively, to a spherical or elongated tubular or conical structure having a diameter or a cross-section of less than about 1,000 nm (spherical structure) or less than about 500 nm (tubular structure). The length of the tubular nanostructure of the present invention is at least about 1 μm.

As used herein the phrase "fibrillar nanostructure" or "nonfibril" refers to a filament or fiber having a diameter or a cross-section of less than about 100 nm. The length of the fibrillar nanostructure of the present invention is preferably at least about 1 μm.

As used herein the phrase "ribbon-like nanostructures" refers to a filament or fiber, packed in a flat ribbon-like structure, having a diameter or a cross-section of less than about 500 nm. The length of the ribbon-like nanostructures of the present invention is preferably at least 1 about μm.

Nanoparticle Conjugates of Diphenylalanine (FF) or Analogs thereof and Active Moieties The present invention relates to a nanoparticle comprising a self-assembled conjugate of a diphenylalanine (FF) dipeptide or analog thereof, covalently bound, directly or through a linker, to a bioactive moiety selected from the group consisting of a therapeutically active agent (i.e., a drug which may be a small molecule or a biologic substance), a cosmetic agent, a cell targeting moiety, a labelling moiety, a radioactive moiety, a cell targeting moiety, an imaging agent and a diagnostic agent. Active moieties suitable for incorporation into the conjugates of the present invention are described hereinbelow.

Figure 1A:
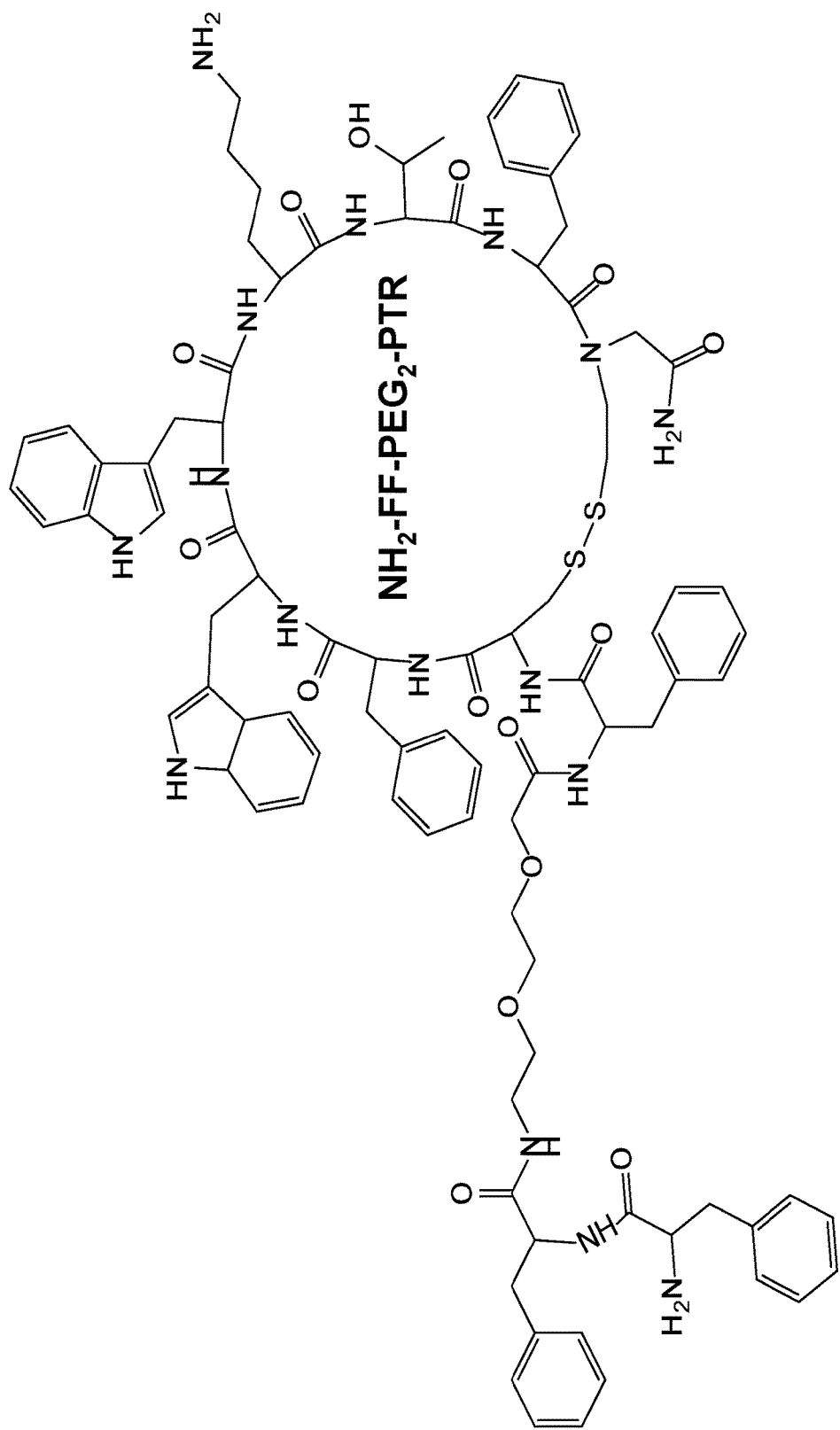
FIG. 1: The chemical structure of PTR conjugates. (a) The hormone analog (PTR) is conjugated to the diphenylalanine motif (FF) via a short polyethylene glycol (PEG$_2$) linker. (b)

In one embodiment, a diphenylalanine (FF) dipeptide is used to generate self-assembled nanoparticle conjugates. In this embodiment, the terminal amino group of the dipeptide is unsubstituted. An example of a conjugate comprising a diphenylalanine (FF) dipeptide is depicted in FIG. 1a.

In other embodiments, a diphenylalanine (FF) dipeptide analog is used to generate self-assembled nanoparticle conjugates. An example of a FF dipeptide analog is a protected FF dipeptide, e.g., an amino-protected dipeptide wherein the terminal amino group is capped with an amino protecting group (or a "N-protecting group", a term used herein interchangeably").

Figure 1B:
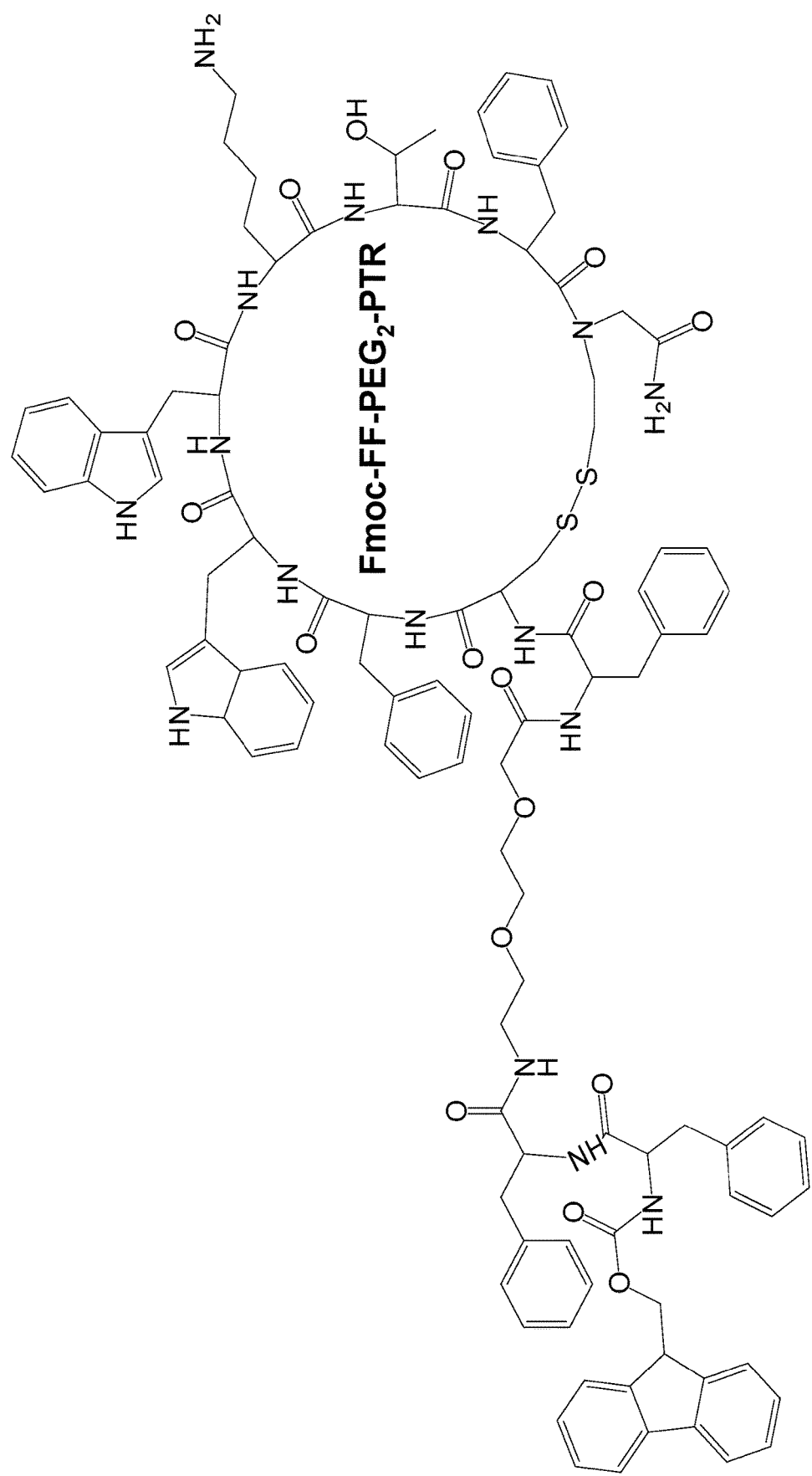

For example, an amino-protected FF dipeptide may be selected from the group consisting oft-butoxycarbonyl-diphenylalanine (Boc-FF), 9-fluorenylmethoxycarbonyl diphenylalanine (Fmoc-FF) and benzyloxycarbonyl (Cbz) diphenylalanine (Cbz-FF). Each possibility represents a separate embodiment of the present invention. An example of a conjugate comprising an Fmoc-diphenylalanine (FF) dipeptide is depicted in FIG. 1b.

Other amino protecting groups can be used to generate amino-protected dipeptides in accordance with the principles of the present invention. Examples of amino-protecting groups include, but are not limited to: acyl (eg., acetyl, phenylcarbonyl), or a silyl group, which can be substituted with alkyl (trialkylsilyl), with an aryl (triarylsilyl) or a combination thereof (e.g., dialkylphenylsilyl), e.g., trimethylsilyl (TMS) or t-butyldimethyl silyl (TBDMS). In accordance with these embodiments, the FF dipeptide may be selected from the group consisting of acyl-phenylalanine (Ac-FF) (e.g., acetyl-FF or phenylcarbonyl-FF), and silyl-phenylalanine (silyl-FF). Each possibility represents a separate embodiment of the present invention.

According to the principles of the present invention, the diphenylalanine (FF) dipeptide or analog thereof is conjugated to the active moiety directly or through a linker, with each possibility representing a separate embodiment of the present invention.

The linker, when present, comprises two or more functional groups capable of linking the diphenylalanine (FF) dipeptide or analog thereof to the active moiety. In some embodiments, the linker may be based on or derived from polyethylene glycol (PEG). In some embodiments, Fmoc-NH-(PEG)$_2$-COOH is used as a starting material (reagent) to link the diphenylalanine (FF) dipeptide or analog thereof to the active moiety. The structure of Fmoc-NH-(PEG)$_2$-COOH is represented below:

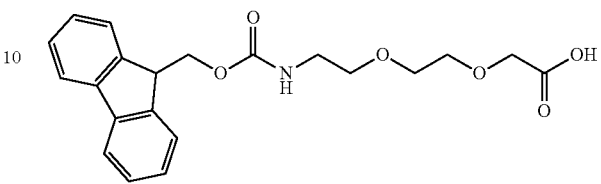

In accordance with this embodiment, the linker moiety that couples the diphenylalanine (FF) dipeptide or analog thereof to the active moiety is represented by the structure, abbreviated herein as "(PEG)$_2$":

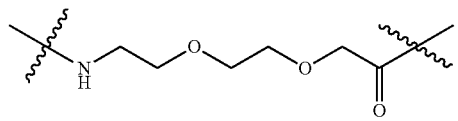 [SMILES: *NCCOCCOCC(*)=O]

However, it is apparent to a person of skill in the art that other linkers, whether PEG-based or not, can be used to couple the diphenylalanine (FF) dipeptide or analog thereof to the active moiety in accordance with the principles of the present invention. For example, the following non-limiting examples of linkers may be used: a linear or branched C1-C20 alkylene, C2-C20 alkenylene, C2-C20 alkynylene or arylene moiety, each of which optionally incorporates one or more heteroatoms (e.g., O, N, S) in the chain, and which is optionally substituted at either end (or both ends) with a group selected from the group consisting of NH—, —C(=O)—, —O—, —S—, —C(=O)—O—, —O—C(=O)—O—, —C(=O)—NH—, —NH—C(=O)—NH—, NH—C(=O)—O—, —S(=O)—, —S(=O)—O—, —PO(=O)—O—, and any combination thereof. Each possibility represents as separate embodiment of the present invention.

In some embodiments, the nanoparticles have a diameter between about 50 nm and about 250 nm.

The nanoparticles of the present invention may self-assemble into a variety of structures, such as nanospheres, nanotubes, nanofibrils and ribbon-like nanostructures. Each possibility represents a separate embodiment of the present invention.

In some specific embodiments, the present invention relates to a somatostatin analog covalently conjugated to FF dipeptide or Fmoc-FF dipeptide. In a specific embodiment, the nanoparticle is represented by the structure:

FF-(PEG)$_2$-PTR wherein PTR is somatostatin or analog thereof, FF is diphenylalanine or analog thereof, and (PEG)$_2$ is a linker derived polyethylene glycol as defined above.

In one specific embodiment, the nanoparticle is represented by the structure depicted in FIG. 1a.

In other embodiments, the nanoparticle is represented by the structure

Fmoc-FF-(PEG)$_2$-PTR wherein PTR is somatostatin or analog thereof, Fmoc-FF is 9-fluorenylmethoxycarbonyl diphenylalanine, and (PEG)$_2$ is a linker derived from polyethylene glycol as defined above.

In one specific embodiment, the nanoparticle is represented by the structure depicted in FIG. 1b.

Supramolecular Co-Assembled Nanoparticles

In accordance with some embodiments of the present invention, supramolecular co-assemblies were designed that include both FF-modified hybrids and FF or FF analog (e.g., Boc-FF) as building block units. FF-modified hybrids are covalently bound to a bioactive moiety to form a conjugate, which is co-assembled with the FF dipeptide or FF dipeptide analog to form co-assembled co-polymeric nanostructures. As detailed above, co-assembly with Boc-FF peptide (or other FF analog) may prevent the steric hindrance between the targeting moieties and be able to function as a spacer to achieve better binding to cancer cells. The Boc-FF moiety (or other FF analog) is co-assembled with the conjugate through non-covalent interactions. Non-covalent interactions may include electrostatic interactions, hydrogen bonding, van der Waals interactions, donor-acceptor interactions, aromatic (e.g., π-π interactions, cation-π interactions and metal-ligand interactions. These interactions lead to the chemical attachment of the material to the conjugate network of the nanostructure.

Thus, in some embodiments, nanoparticle formed by supramolecular co-assembly of the self-assembled conjugates described above, and a diphenylalanine (FF) dipeptide or analog thereof. The diphenylalanine (FF) dipeptide is preferably co-assembled with the conjugate through non-covalent interactions. In some embodiments, the diphenylalanine (FF) dipeptide or analog thereof is selected from the group consisting of diphenylalanine (FF), an amino-protected diphenylalanine (FF), a carboxy-protected diphenylalanine (FF), or a FF dipeptide protected at both the amino and carboxy terminus.

Any of the N-protected FF dipeptides described above can be used to form supramolecular co-assemblies as described herein. Examples of preferred N-protected diphenylalanine dipeptides are t-butoxycarbonyl-diphenylalanine (Boc-FF), 9-fluorenylmethoxycarbonyl diphenylalanine (Fmoc-FF), benzyloxycarbonyl (Cbz) diphenylalanine (Cbz-FF), acyl diphenylalanine (Ac-FF) and silyl diphenylalanine (silyl-FF). Each possibility represents a separate embodiment of the present invention.

A carboxy-protected diphenylalanine (FF) is a dipeptide wherein the terminal carboxy group is capped with a carboxy protecting group. Representative carboxy-protecting groups that can be used to generate carboxy-protected dipeptides include, but are not limited to, methyl, ethyl, t-butyl, benzyl (Bn), p-methoxybenzyl (PMB), 9-fluorenylmethyl (Fm), trimethylsilyl (TMS), t-butyldimethylsilyl (TBDMS), diphenylmethyl (benzhydryl, DPM) and the like. Each possibility represents a separate embodiment of the present invention.

Another example of a FF dipeptide analog is a dipeptide wherein both the terminal carboxy group and the amino groups are protected with their respective protecting groups as defined above.

In some embodiments, the ratio between the conjugate and the diphenylalanine (FF) dipeptide is about 1 to about 10, preferably about 1 to about 4. Each possibility represents a separate embodiment of the present invention.

In some embodiments, the co-assembled nanoparticles have a diameter between about 50 nm to about 250 nm, as measured by dynamic light scattering (DLS). The nanoparticles may self-assemble into a variety of structures, such as nanospheres, nanotubes, nanofibrils and ribbon-like nanostructures. Each possibility represents a separate embodiment of the present invention.

In a specific embodiment, the present invention relates to a somatostatin analog covalently conjugated to Fmoc-FF, co-assembled with Boc-FF. In some embodiments, the conjugate is represented by the structure:

Fmoc-FF-(PEG)$_2$-PTR:Boc-FF (1:4)

wherein PTR is somatostatin or analog thereof, Fmoc-FF is 9-fluorenylmethoxycarbonyl diphenylalanine, Boc-FF is t-butoxycarbonyl diphenylalanine, and (PEG)$_2$ is a linker based on polyethylene glycol, and wherein Fmoc-FF-(PEG)$_2$-PTR is represented by the structures as depicted in FIG. 1b. The "1:4" ratio means the ratio between the Fmoc-FF-(PEG)$_2$-PTR and Boc-FF components of the conjugate. This supramolecular structure is depicted schematically in FIG. 2b.

Bioactive Moieties

Bioactive moieties that can be incorporated into the conjugates of the present invention include, for example, therapeutically active agents (i.e., drugs which may be small molecules or biologics), cosmetic agents, diagnostic agents, biological substances, cell targeting moieties, radioactive moieties, imaging agents and labeling moieties. More particular examples include, but are not limited to, drugs, peptides, polypeptides, proteins, enzymes, hormones, growth factors, nucleic acids, organisms such as bacteria, fluorescence compounds or moieties, phosphorescence compounds or moieties, radioactive compounds or moieties, and inorganic nanoparticles useful for biological applications. Each possibility represents a separate embodiment of the present invention.

In some embodiments, the active moiety is selected from the group consisting of peptides, polypeptides, polymers, and any combination thereof. In one particular embodiment, the active moiety is an anti-cancer drug, for example a hormone or hormone analog. Each possibility represents a separate embodiment of the present invention. In a currently preferred embodiment, the hormone analog is a somatostatin analog.

As used herein, the phrase "therapeutically active agent" describes a chemical substance, which exhibits a therapeutic activity when administered to a subject. These include, as non-limiting examples, chemotherapeutic agents, anti-proliferative agents, anti-cancer agents, inhibitors, ligands (e.g., receptor agonists or antagonists), co-factors, anti-inflammatory drugs (steroidal and non-steroidal), antipsychotic agents, analgesics, anti-thrombogenic agents, anti-platelet agents, anticoagulants, anti-diabetics, statins, toxins, antimicrobial agents, anti-histamines, metabolites, anti-metabolic agents, vasoactive agents, vasodilator agents, cardiovascular agents, antioxidants, phospholipids, and heparins, to name a few.

As used herein, the phrase "biological substance" refers to a substance that is present in or is derived from a living organism or cell tissue. Representative examples include, without limitation, amino acids, peptides, proteins, oligonucleotides, nucleic acids, genes, hormones, growth factors, enzymes, co-factors, antisense molecules, antibodies, antigens, vitamins, immunoglobulins, cytokines, prostaglandins, vitamins, toxins and the like, as well as organisms such as bacteria, viruses, fungi and the like.

As used herein, the phrase "diagnostic agent" describes an agent that upon administration exhibits a measurable feature that corresponds to a certain medical condition. These include, for example, labeling compounds or moieties, as is detailed hereunder. As used herein, the phrase "labeling compound or moiety" describes a detectable moiety or a probe which can be identified and traced by a detector using known techniques such as spectral measurements (e.g., fluorescence, phosphorescence), electron microscopy, X-ray diffraction and imaging, positron emission tomography (PET), single photon emission computed tomography (SPECT), magnetic resonance imaging (MRI), computed tomography (CT) and the like.

Representative examples of labeling compounds or moieties include, without limitation, chromophores, fluorescent compounds or moieties, phosphorescent compounds or moieties, contrast agents, radioactive agents, magnetic compounds or moieties (e.g., diamagnetic, paramagnetic and ferromagnetic materials), and heavy metal clusters, as is further detailed hereinbelow, as well as any other known detectable moieties.

As used herein, the term "chromophore" refers to a chemical moiety or compound that when attached to a substance renders the latter colored and thus visible when various spectrophotometric measurements are applied. A heavy metal cluster can be, for example, a cluster of gold atoms used, for example, for labeling in electron microscopy or X-ray imaging techniques.

As used herein, the phrase "fluorescent compound or moiety" refers to a compound or moiety that emits light at a specific wavelength during exposure to radiation from an external source. Non-limiting examples of a fluorescent compound is fluorescin or carboxy-fluorescin. As used herein, the phrase "phosphorescent compound or moiety" refers to a compound or moiety that emits light without appreciable heat or external excitation, as occurs for example during the slow oxidation of phosphorous.

As used herein, the phrase "radioactive compound or moiety" encompasses any chemical compound or moiety that includes one or more radioactive isotopes. A radioactive isotope is an element which emits radiation. Examples include α-radiation emitters, β-radiation emitters or γ-radiation emitters. Suitable radionuclides for use as radioactive agents include, but are not limited to, Carbon-11, Fluorine-18, Bromine-76, or Iodine-123, and Iodine-124 and metallic radionuclides include Antimony-124, Antimony-125, Arsenic-74, Barium-103, Barium-140, Beryllium-7, Bismuth-206, Bismuth-207, Cadmium-109, Cadmium-115m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-67, Erbium-169, Europium-152, Gallium-64, Gallium-68, Gadolinium-153, Gadolinium-157 Gold-195, Gold-199, Hafnium-175. Hafnium-175-181, Holmium-166, Indium-110, Indium-111, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185+191, Palladium-103, Platinum-195m, Praseodymium-143, Promethium-147, Protactinium-233, Radium-226, Rhenium-186, Rhenium-188, Rubidium-86, Ruthenium-103, Ruthenium-106, Scandium-44, Scandium-6, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Tin-114, Tin-117m, Titanium-44, Tungsten-185, Vanadium-48, Vanadium-49, Ytterbium-169, Yttrium-86, Yttrium-88, Yttrium-90, Yttrium-91, Zinc-65, and Zirconium-95. In certain embodiments the radionuclide is selected from for example 99mTechnetium, 201Thalium, 111Indium, 67Gallium, 90Yttrium, 177Lutetium, and 123Iodine.

Inorganic nanoparticles may include metal nanoparticles such as gold (Au) nanoparticles.

Therapeutic Uses

In other aspects, the present invention further relates to a nanoparticle as described herein, for use for the delivery of drugs.

In other embodiments the present invention further relates to a nanoparticle as described herein, for use as a targeting agent for delivery of anti-cancer drugs to a target tumor.

In other embodiments the present invention further relates to a nanoparticle as described herein, for use as an imaging agent.

In other embodiments, the present invention relates to the use of diphenylalanine (FF) or an analog thereof, for assembling a peptide, polypeptide or protein into a nanometric structure so as to enhance the half-life of said peptide, polypeptide or protein in a biological sample. In some embodiments, the diphenylalanine (FF) dipeptide or analog thereof is FF, Fmoc-FF or Boc-FF, which is used to enhance the half-life of a protein in the body of a subject.

The conjugates of the present invention may be used as drug delivery agents to target an anti-cancer drug to the target tumor. Thus, in some embodiments, the present invention relates to an anti-cancer drug covalently conjugated to FF dipeptide or analog thereof, as described above, for use as a delivery system of chemotherapy to a target tumor. In one specific embodiment, the present invention relates to a somatostatin analog covalently conjugated to FF dipeptide or a FF dipeptide analog as described above for use as a delivery system of chemotherapy to a target tumor. In another specific embodiment, the present invention relates to a somatostatin analog covalently conjugated to FF dipeptide or FF dipeptide analog as described above, for use as a delivery system of chemotherapy in pancreatic cancer.

As contemplated herein, it is hypothesized that co-assembly of the conjugates of the presentation with FF-dipeptides may prevent the steric hindrance between the targeting moieties by functioning as a spacer to achieve better binding to cancer cells. Indeed, as demonstrated herein, conjugates which are co-assembled with FF dipeptides were shown to efficiently bind cancer cells and selectively accumulate in the tumor, thereby playing a dual role of both a nanocarrier and a bioactive targeting component.

Thus, in some embodiments, the present invention relates to an anti-cancer drug covalently conjugated to FF dipeptide or analog thereof, co-assembled with a FF dipeptide or analog thereof as described above, for use as a delivery system of chemotherapy to a target tumor. In one specific embodiment, the present invention relates to a somatostatin analog covalently conjugated to FF or analog thereof, co-assembled with FF or analog thereof as described above, for use as a delivery system of chemotherapy to a target tumor. In another specific embodiment, the present invention relates to a somatostatin analog covalently conjugated to FF or analog thereof, co-assembled with FF or analog thereof as described above, for use as a delivery system of chemotherapy in pancreatic cancer.

Pharmaceutical Compositions

In additional embodiments the present invention further relates to pharmaceutical composition comprising the nanoparticle as described herein, and a pharmaceutically or cosmetically acceptable carrier. The present invention further relates to a nanoparticle as described herein, for use in the preparation of pharmaceutical composition.

As used herein, a "pharmaceutical composition" refers to a preparation of the nanostructures described herein (including the conjugates or the co-polymers incorporating such conjugates), with other chemical components such as acceptable and suitable carriers and excipients. The purpose of a pharmaceutical composition is to facilitate administration of a compound to an organism. Hereinafter, the term "pharmaceutically, or cosmetically acceptable carrier" refers to a carrier or a diluent that does not cause significant irritation to an organism and does not abrogate the biological activity and properties of the applied compound. Examples, without limitations, of carriers include propylene glycol, saline, emulsions and mixtures of organic solvents with water, as well as solid (e.g., powdered) and gaseous carriers.

The compositions described herein may be formulated in conventional manner using one or more acceptable carriers comprising excipients and auxiliaries, which facilitate processing of the nanoparticles into preparations. Proper formulation is dependent upon the route of administration chosen. Techniques for formulation and administration of drugs may be found in "Remington's Pharmaceutical Sciences," Mack Publishing Co., Easton, Pa., latest edition.

The pharmaceutical compositions described herein can be formulated for various routes of administration. Suitable routes of administration may, for example, include oral, sublingual, inhalation, rectal, transmucosal, transdermal, intracavemosal, topical, intestinal or parenteral delivery, including intramuscular, subcutaneous and intramedullary injections as well as intrathecal, direct intraventricular, intravenous, intraperitoneal, intranasal, or intraocular injections.

Formulations for topical administration include but are not limited to lotions, ointments, gels, creams, suppositories, drops, liquids, sprays and powders. Conventional carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable. Formulations for parenteral administration may include, but are not limited to, sterile solutions which may also contain buffers, diluents and other suitable additives. Timed oral compositions are envisaged for treatment.

The nanostructures of the present invention can also be incorporated into medical devices. The medical devices incorporating the nanostructures of the present invention may include an implant, an artificial body part, a tissue engineering and regeneration system, a wound dressing, a synthetic skin, a cell culture matrix, a protein microarray chip, a biosensor, an anastomotic device (e.g., stent), a sleeve, a film, a scaffold and a coating.

Methods of Preparing

The nanostructures of the present invention are preferably generated by allowing a solution of the FF-dipeptides of the present invention to self-assemble under mild conditions as detailed in Example 1 of the Examples section which follows.

In additional embodiments, the present invention relates to a method of preparing the nanoparticle described herein, the method comprising the step of covalently conjugating a bioactive moiety, directly or through a linker, to diphenylalanine (FF) dipeptide or analog thereof, under conditions sufficient to form a self-assembled conjugate.

In other embodiments, the present invention relates to a method of preparing the supramolecular co-assembled nanoparticle as described herein, the method comprising the steps of: (a) covalently conjugating said active moiety, directly or through a linker, to diphenylalanine (FF) dipeptide or analog thereof, under conditions sufficient to form a self-assembled conjugate; and (b) contacting the product of step (a) with diphenylalanine (FF) dipeptide or analog thereof, under conditions sufficient to form a supramolecular structure, wherein the diphenylalanine (FF) or analog thereof is co-assembled with the conjugate of step (a) through non-covalent interactions.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting. As used herein, the singular form "a," "an," and "the" include plural references unless the context clearly dictates otherwise. For example, the term "a compound" or "at least one compound" may include a plurality of compounds, including mixtures thereof.

The foregoing examples of the related art and limitations related therewith are intended to be illustrative and not exclusive. Other limitations of the related art will become apparent to those of skill in the art upon a reading of the specification and a study of the figures.

All references cited herein are hereby incorporated by references in their entirety herein.

EXAMPLES

Example 1

Design and Synthesis of Diphenylalanine-Somatostatin (FF-PTR) Peptides

Figure 1C:
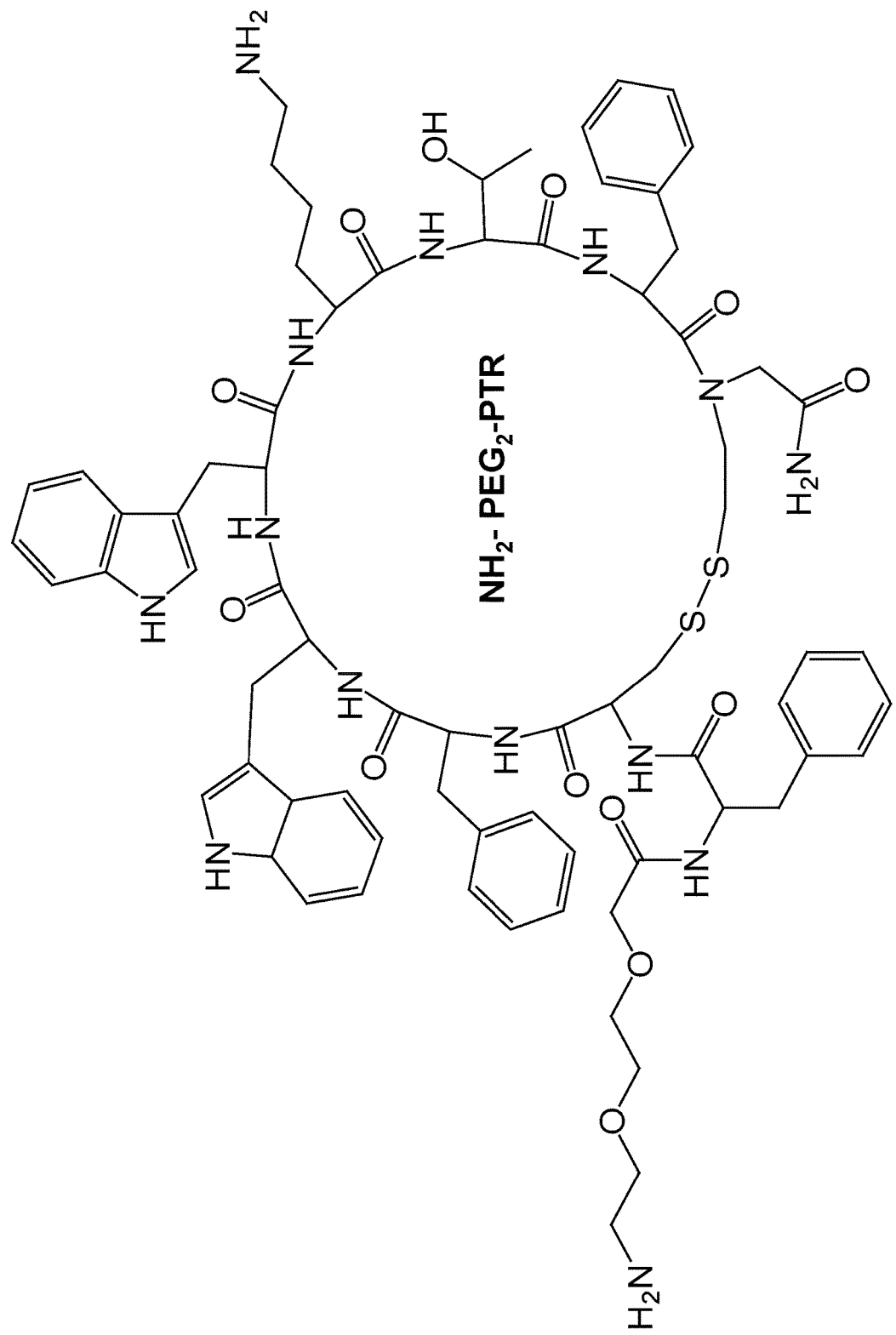

The FF-PTR peptides were designed and synthesized by solid phase peptide synthesis (SPPS) using disulfide backbone cyclization. The somatostatin analogs were synthesized according to the highly stable and tumor-selective PTR 3207 sequence[22] and conjugated to the FF via $PEG_2$ linker (FIG. 1a). In addition, Fmoc amine protecting group was employed to allow the formation of varied nanostructures (FIG. 1b). Fmoc-protected amino acids and short peptides, such as the Fmoc-FF and other Fmoc dipeptides, have been shown to form rigid macroscopic nanostructures and hydrogels. A control analog lacking the FF moiety was also synthesized. As expected, it did not form any ordered nanostructures (FIG. 1c).

Nanotubes were formed by solvent switch method in which FF peptide powder was dissolved in an organic solvent, hexafluoro-iso-propanol (HFIP), then diluted into water.[1] Thus, FF-PTRs were dissolved in HFIP to allow comparable structural organization. Transmission electron microscopy (TEM) images revealed that both Fmoc-FF-$PEG_2$-PTR and $NH_2$-FF-$PEG_2$-PTR conjugates formed nanospheres (NS) in 10% $HFIP/H_2O$ solution (FIG. 3a, 3b). While screening for biocompatible conditions for the formation of homogeneous nanospheres population, solutions of FF-PTR were prepared in various solvents, such as dimethyl sulfoxide (DMSO), acetic acid, as well as ethanol in different concentrations. TEM images demonstrated the formation of spherical structures, under these conditions (FIGS. 11 and 12), similar to those formed by FF peptide derivatives and hybrids. The integration of the FF unit to the somatostatin cyclic analog enabled the formation of self-assembled spherical nanostructures. When ethanol was used, the FF-PTR peptides form mostly spheres. FF-PTRs in 10% ethanol/$H_2O$ self-assembled into nanospheres that were homogenous in shape and size with a diameter of 50-200 nm (FIG. 4a, 4b), an optimal size for tumor targeting utilizing the EPR effect. Notably, the peptide which lacks the FF unit, $NH_2$-$PEG_2$-PTR, did not form ordered structures (FIG. 4c). Furthermore, practically no aggregates were observed under these conditions.

Example 2

Co-Assembly of FF-PTR Peptides with Boc-FF

Fmoc-FF-$PEG_2$-PTR prepared per Example 1 was co-assembled with Boc-FF to form supramolecular co-polymers, formed on the basis of non-covalent bonds. The co-assembly is envisioned to enable separation and physical distance between the cell binding moieties. When Boc-FF is dissolved in 10% ethanol/$H_2O$, mostly nanotubes are formed (FIG. 4d).[20-24] However, mixing both Boc-FF and Fmoc-FF-$PEG_2$-PTR, under the same conditions at different molar ratios of 2:1, 4:1 and 10:1, resulted in the mere assembly of spherical structures as confirmed by TEM analysis (FIG. 4e-4g). The peptides co-assemblies were prepared at different molar ratios of 1:2, (1:4) and 1:10. The nanospheres ultrastructures were confirmed by TEM analysis (FIG. 4e-4g). Based on these experiments, it was concluded that the ability of Fmoc-FF-$PEG_2$-PTR to form spheres had also affected the spherical co-assembly of Boc-FF peptide. As expected, co-assembly of peptide lacking the FF motif with Boc-FF did not form ordered nanostructures (FIG. 4h).

The Fmoc-FF-$PEG_2$-PTR:Boc-FF (1:4) co-assembled spheres were further characterized by atomic force microscopy (AFM) (FIG. 5). As demonstrated, the nanostructures were uniform and spherical in shape (FIG. 5a, 5b) with a size range of 20-90 nm (FIG. 5c).

The hydrodynamic diameter of the diphenylalanine co-assembled nanospheres Boc-FF:Fmoc-FF-$PEG_2$-PTR 4:1 as monitored using dynamic light scattering (DLS) showed a remarkable organization of the nanostructures. Compared to the non-homogenous size of each of the Fmoc-FF-$PEG_2$-PTR and Boc-FF nanostructures, the mixture of Fmoc-FF-$PEG_2$-PTR and Boc-FF intriguingly resulted in the formation of more homogenously disperse spheres with no aggregates and an average diameter of 167±82 nm (FIG. 6) with a polydispersity index of 0.148. These results are in correlation to the sphere diameter measured by TEM. Remarkably, the mixture between Fmoc-FF-$PEG_2$-PTR and Boc-FF formed more homogenously disperse spheres with no aggregates, compared to the one component assemblies. The obtained size of the co-assembled particles ranges between the sizes of the particles formed by each one of the peptides (FIG. 6).

The results demonstrate that mixing two aromatic peptides known to self-assemble into different nanostructures resulted in formation of new spherical structures displaying new physical properties. The ability of Fmoc-FF-$PEG_2$-PTR to form spheres directed the spherical co-assembly of the Boc-FF peptide.

Example 3

Use of Fmoc-FF-$PEG_2$-PTR and Fmoc-FF-$PEG_2$-PTR:Boc-FF (1:4) Co-Assembled Nanospheres as Encapsulation Agents Encapsulation of therapeutic and contrast agents into nanospheres provides efficient drug delivery and imaging capacity while maintaining reduced side effects. Thus, the nanospheres formed by the assembly of Fmoc-FF-$PEG_2$-PTR and by the Fmoc-FF-$PEG_2$-PTR:Boc-FF (1:4) co-assembled nanospheres, were tested for their ability to encapsulate carboxyfluorescein (CF) and gold nanoparticles (AuNPs). Carboxyfluorescein, a common fluorescent tracer agent, was also encapsulated within the peptide assemblies as can be observed in the stimulated emission depletion (STED) microscopy images (FIG. 7a, 7b). The carboxyfluorescein was encapsulated in both Fmoc-FF-$PEG_2$-PTR (FIG. 7a) and Fmoc-FF-$PEG_2$-PTR:Boc-FF (1:4) nanospheres (FIG. 7b). In addition, AuNPs are the most commonly used inorganic nanoparticles for biological applications, due to their physical and chemical properties. AuNPs have been mostly used for labeling and imaging applications and are often used as contrast agents for TEM.[25, 26] The TEM images showed that all of the 5 nm AuNPs were encapsulated inside the nanospheres (FIG. 7c, 7d).

Example 4

Binding of Fmoc-FF-$PEG_2$-PTR and Fmoc-FF-$PEG_2$-PTR:Boc-FF (1:4) Co-Assembled Nanospheres to Cancer Cells To verify the binding capacity of the nanospheres to cancer cells, the Fmoc-FF-$PEG_2$-PTR and Fmoc-FF-$PEG_2$-PTR:Boc-FF (1:4) nanospheres were incubated with human pancreatic cancer cells (Panc-1), and their binding ability was observed by confocal microscopy. Carboxyfluorescein was encapsulated during the preparation of the nanoparticles. Following two hours of incubation with Panc-1 cancer cells, the cells were treated with concanavalin A (Con A) Alexa Fluor 647 conjugate. Live cell imaging analysis was performed by confocal microscopy (FIGS. 8 and 13). As demonstrated in FIG. 8a and in FIG. 13, green fluorescence was observed in the cytoplasm of the cells that were treated with the co-assembled (1:4) spheres. The particles were still partially bound to the membrane, indicating that the internalization of the particles was slower than the uptake of the positive control, the covalently fluorescent labeled somatostatin analog, PTR-3207 (FIG. 8b), suggesting that this slow uptake is due to the large size of the particles compared to the PTR 3207 peptide. However, no fluorescence was observed either when carboxyfluorescein loaded Fmoc-FF-$PEG_2$-PTR spheres or when a mixture of carboxyfluorescein and BocFF were used (FIG. 8c, 8d). These findings support the proposed model for the co-assembly of the two peptides. As assumed, the co-assembly with Boc-FF which serves as a spacer, enabled the binding of PTR analog to the somatostatin receptor (FIG. 2b). No fluorescence was observed also with control samples treated either with free carboxyfluorescein or ethanol (FIG. 8e, 8f).

Furthermore, incubation of human embryonic kidney (HEK-293) cells, which do not overexpress the SSTRs, resulted in a significant decrease of (1:4) nanospheres uptake (FIG. 14). These results indicate that the internalization is receptor mediated.

Example 5

Biodistribution of Fmoc-FF-$PEG_2$-PTR:Boc-FF (1:4) Co-Assembled Nanospheres in Tumors The biodistribution of carboxyfluorescein loaded co-assembled (1:4) spheres was measured 24 hours post IV injection of Panc-1 xenografts into the tail vein of wild type mice musing fluorescence microscopy, as measured by macto-imaging systems. These analyses demonstrated highly preferred enhanced selective accumulation of the co-assembled nanospheres in the tumor compared to PTR 3207-86 (FIG. 9). The fluorescence detected in the tumor was at least 92-fold higher than in the normal tissues. The minor fluorescence in the kidneys was most probably due to renal excretion. A negligible amount of the fluorescence was also detected in the liver, suggesting hepatic clearance of particles. No fluorescence was detected in the pancreas and in spleen (FIG. 9C).

Conclusions

Taken together, the results demonstrate the the assembly and the co-assembly of diphenylalanine-hormone analog conjugates into supramolecular nanostructures. As demonstrated herein, the introduction of the simple diphenylalanine recognition module induces the assembly of the hybrid peptide to form nanospheres. Furthermore, supramolecular co-polymers with such functional designed building block mixed with a FF derivative was shown to efficiently bind cancer cells and selectively accumulate in the tumor. Therefore, these supramolecular structures could play a dual role of both a nanocarrier and a bioactive targeting component. These findings present a new strategy for drug delivery which could be used for engineering additional targeting analogs, as well as for the design and synthesis of more complex co-assembled nanoparticles. Other targeting moieties, imaging agents and drugs could be conjugated to the FF motif and co-assembled into multi-functionalized supramolecular co-polymers to deliver theranostics to cancer cells. FF-based assemblies and co-assemblies could be designed with other biological and chemical moieties for various applications, such as ultra-sensitive sensors, tissue engineering scaffold as well as chemical catalysis.

Example 6

Materials and Methods

Materials

All chemicals and solvents were A.R. grade or purified by standard techniques. Chemical reagents were purchased from Sigma-Aldrich. HPLC grade solvents were purchased from Bio-Lab (Jerusalem, Israel). Materials and reagents for peptide synthesis were purchased from Merck, Anaspec and D-Chem. All tissue culture reagents were purchased from Biological Industries Ltd (Beit Haemek, Israel). Cells were kindly provided by Prof. A. Orenstein (Advanced Technology Center, Sheba Medical Center, Tel Hashomer, Israel).

Design and Synthesis of PTR Conjugates

The FF-PTR peptides and control PTR peptides which do not bear the diphenylalanine residue were synthesized by solid-phase peptide synthesis (SPPS). GlyS2 Building unit bearing thiol functional group was synthesized according to Gazal et al.[27] Couplings were performed according to previously described methods.[27-29] Removal of protecting groups, cyclization and cleavage were performed as described by Falb et al. [29]

Preparative HPLC-based purification method was developed for each peptide conjugate. The preparative RP-HPLC was performed on a Sapphire instrument using a preparative column (LiChrospher 100 RP-18 (5 μm) Hibar column 250 mm×25 mm) and a flow rate of 30 mL min$^{-1}$ and water/acetonitrile (each containing 0.1% TFA) gradient.

Preparation of PTR-FF Nanospheres

PTR conjugates were dissolved in various solvents such as HFIP, DMSO, ethanol and acetic acid to a concentration of 3-60 mM. Then the stock solution was immediately diluted in ultra-pure water (UPW) to a final concentration of 0.3-6 mM.

Preparation of the Co-Assembled Nanospheres

Boc-FF was dissolved in ethanol to a concentration of 12 mM. Then it was mixed in different ratios with the Fmoc-FF-PEG$_2$-PTR stock solution. The mixture was diluted immediately in UPW to a final concentration of 0.3 mM Fmoc-FF-PEG$_2$-PTR.

Transmission Electron Microscopy (TEM)

The conjugate peptides were dissolved as described above at a concentration of 6 mM and then diluted with UPW to a final concentration of 0.12-3 mM Immediately after dilution in UPW, 5 μL of the peptide solution was placed on a 200-mesh copper grid. After 2 min, excess fluid was removed and then negatively stained by covering the grid with 5 μL of 2% uranyl acetate in UPW. After 2 min, excess uranyl acetate solution was removed. Samples were viewed using a JEOL 1200EX TEM operating at 80 kV.

Atomic Force Microscopy (AFM)

AFM analysis was performed using Asylum MFP-1D AFM instrument (Asylum Research, Santa Barbara, Calif., USA). To obtain force data for Fmoc-FF-PEG2-PTR:Boc-FF (1:4) (0.3 mM and 1.2 mM respectively), the sample was prepared as described above. 5 μL of a freshly prepared sample was deposited on cleaved mica and dried at room temperature. Force measurements of the samples were conducted using a SiO$_2$ colloidal probe (tip velocity 1000 nm/s, compressive force of 20 nN).

Dynamic Light Scattering (DLS)

DLS measurements were performed at 25° C. using a Malvern Zetasizer NanoZS instrument, equipped with a 532 nm laser at a fixed scattering angle of 90°. Conjugate solutions (0.3 mM) were prepared as was described earlier. Size distribution was measured (diameter, nm) for each conjugate (at least three measurements for each sample were recorded).

Carboxyfluorescein and Gold Nanoparticles Encapsulation

Carboxyfluorescein was dissolved in UPW and then added to a solution of Fmoc-FF-PEG$_2$-PTR:Boc-FF (1:4) in ethanol to a final concentration of 15 μM carboxyfluorescein, 0.3 mM Fmoc-FF-PEG2-PTR, 10% ethanol. Free carboxyfluorescein was filtered with 10% ethanol by centricon filtration, 50 KDa cutoff (Millipore). The fluorescent spheres were examined using stimulated emission depletion (STED) microscopy.

5 nm AuNPs dispersed in aqueous solution (Sigma) were diluted in UPW and then were added to a solution of Fmoc-FF-PEG$_2$-PTR:Boc-FF (1:4) in ethanol to a final concentration of 50% AuNPs, 0.3 mM Fmoc-FF-PEG$_2$-PTR, 10% ethanol. The obtained co-assembled spheres were examined using TEM.

Live Cell Imaging Through Confocal Microscopy

Panc-1 and HEK-293T cells were cultured (100,000 cells) on a cell culture dish with a glass bottom (35 mm, Greiner Bio-one). In the following day cells were incubated for two hours at 37° C. under various conditions: carboxyfluorescein (15 μM), Boc-FF (0.12 mM) and carboxyfluorescein (15 μM), Fmoc-FF-PEG$_2$-PTR (0.3 mM) encapsulated with carboxyfluorescein (15 μM), PTR-3207-86 (0.3 mM), Fmoc-FF-PEG$_2$-PTR (0.3 mM):Boc-FF (1:4) nanospheres encapsulated with carboxyfluorescein (15 μM). After incubation, cells were washed with PBS buffer and were treated with 10 μg/ml Concanavalin A (Con A) Alexa Fluor 647 Conjugate (Invitrogen, Carlsbad, Calif.) for 15 minutes and washed again with PBS. Live cell imaging was conducted using LSM 510 Meta confocal laser scanning microscope (Carl Zeiss, Jena, Germany).

Animals and Tumor Model

An animal model was generated by subcutaneous inoculation of PANC-1 cells and tumor growth was monitored over time. The procedure followed for animal model implementation consisted of growing Panc-1 cells in culture. Male BALB/c athymic nude mice, ~8 weeks of age, were purchased from Harlan Ltd. (Jerusalem, Israel) and maintained under pathogen-limited conditions. Food and water were supplied ad libitum. Tumors were induced by subcutaneous injection of $1.5\times10^7$ Panc-1 human pancreatic carcinoma cells in saline suspension into the groin area of the mice. The tumor volume was calculated using the formula $(L\times W2)/2$ where L is the longest diameter (in mm) of the tumor and W is the longest perpendicular diameter with respect to L. Both values were measured with a caliper. Experiments were started when tumor diameter was approximately 10 mm diameter, after 8-10 weeks post-inoculation. Experimental procedures were performed on animals anesthetized by intraperitoneal injection of 80/20 mg/kg ketamine/xylazine mixture in saline. All experiments were conducted in compliance with regulations of the Animal Welfare Committee at the Sheba Medical Center.

Ex-Vivo Imaging

Panc-1 tumor-bearing mice (n=3) were injected intravenously into the tail vein with Fmoc-FF-PEG$_2$-PTR:Boc-FF 1:4 (FF-CANS 1:4, 100 µl of a 1.5 mM solution) or with control PTR 3207-86 (300 µl of a 0.57 mM solution). 24 hr post injection the tumor and organs were resected and imaged by fluorescent microscope and Cri Maestro as described above.

Fluorescence images were obtained 24 hours post administration. Tumor, spleen, liver, lung, kidney and pancreas, were excised and placed onto a Petri dish, Fluorescence images of excised tissues were obtained immediately using fluorescence inverted microscope (Olympus IX81, Japan) equipped with a digital color camera (Olympus DP71, Japan) at ×100 magnification and 100 ms exposure. After microscopy, tissues were kept at −80° C. until quantitative measurements by CRI Maestro Imaging system.

Quantitative measurements of fluorescence intensities of excised tissue samples were acquired by using a CRI Maestro Imaging system (Cambridge Research & Instrumentation, Inc., Woburn, Mass.) ($\lambda$ex=455 nm, $\lambda$em=515 nm) and analyzed following auto-fluorescence and background signals elimination by spectral analysis carboxyfluorescein.

It is appreciated by persons skilled in the art that the present invention is not limited by what has been particularly shown and described hereinabove. Rather the scope of the present invention includes both combinations and subcombinations of various features described hereinabove as well as variations and modifications. Therefore, the invention is not to be constructed as restricted to the particularly described embodiments, and the scope and concept of the invention will be more readily understood by references to the claims, which follow.

REFERENCES

1. Reches, M. and E. Gazit, *Casting metal nanowires within discrete self-assembled peptide nanotubes*. Science, 2003. 300(5619): p. 625-627.
2. Reches, M. and E. Gazit, *Formation of closed-cage nanostructures by self-assembly of aromatic dipeptides*. Nano Lett, 2004. 4(4): p. 581-5.
3. Song, Y., et at., *Synthesis of peptide-nanotube platinum-nanoparticle composites*. Chem Commun (Camb), 2004 (9): p. 1044-5.
4. Mahler, A., et al., *Rigid, self-assembled hydrogel composed of a modified aromatic dipeptide*. Adv Mater, 2006. 18(11): p. 1365-1370.
5. Gazit, E., *Self-assembled peptide nanostructures: the design of molecular building blocks and their technological utilization*. Chem Soc Rev, 2007. 36(8): p. 1263-1269.
6. Adler-Abramovich, L. and E. Gazit, *Controlled patterning of peptide nanotubes and nanospheres using inkjet printing technology*. J Pept Sci, 2008. 14(2): p. 217-223.
7. Adler-Abramovich, L., et al., *Self-assembled arrays of peptide nanotubes by vapour deposition*. Nat Nanotechnol, 2009. 4(12): p. 849-854.
8. Adler-Abramovich, L., et al., *Patterned arrays of ordered peptide nanostructures*. J Nanosci Nanotechnol, 2009. 9(3): p. 1701-1708.
9. Yan, X., P. Zhu, and J. Li, *Self-assembly and application of diphenylalanine-based nanostructures*. Chem Soc Rev, 2010. 39(6): p. 1877-1890.
10. Gour, N., A. K. Barman, and S. Verma, *Controlling morphology of peptide-based soft structures by covalent modifications*. J Pept Sci, 2012. 18(6): p. 405-412.
11. Fichman, G. and E. Gazit, *Self-assembly of short peptides to form hydrogels: design of building blocks, physical properties and technological applications*. Acta Biomater, 2014. 10(4): p. 1671-1682.
12. Adler-Abramovich, L. and E. Gazit, *The physical properties of supramolecular peptide assemblies: from building block association to technological applications*. Chem Soc Rev, 2014. 43(20): p. 6881-93.
13. Frederix, P. W. J. M., et al., *Exploring the sequence space for (tri-) peptide self-assembly to design and discover*. Nature Chemistry, 2015. 7(1): p. 30-37.
14. Zhou, M., et al., *Self-assembled peptide-based hydrogels as scaffolds for anchorage-dependent cells*. Biomaterials, 2009. 30(13): p. 2523-30.
15. Sedman, V. L., et al., *Tuning the mechanical properties of self-assembled mixed-peptide tubes*. Journal of Microscopy, 2013. 249(3): p. 165-172.
16. Zhang, S., *Fabrication of novel biomaterials through molecular self-assembly*. Nat Biotechnol, 2003. 21(10): p. 1171-8.
17. Orbach, R., et al., *Self-assembled Fmoc-peptides as a platform for the formation of nanostructures and hydrogels*. Biomacromolecules, 2009. 10(9): p. 2646-51.
18. Reches, M. and E. Gazit, *Biological and chemical decoration of peptide nanostructures via biotin-avidin interactions*. J Nanosci Nanotechnol, 2007. 7(7): p. 2239-2245.
19. Castillo, J. J., et al., *Synthesis and characterization of covalent diphenylalanine nanotube-folic acid conjugates*. J Nanopart Res, 2014. 16(7).
20. Keskin, O. and S. Yalcin, *A review of the use of somatostatin analogs in oncology*. Onco Targets Ther, 2013. 6: p. 471-483.
21. Barbieri, F., et al., *Peptide receptor targeting in cancer: the somatostatin paradigm*. Int J Pept, 2013. 2013: p. 926295.
22. Kostenich, G., et al., *Targeting small-cell lung cancer with novel fluorescent analogs of somatostatin*. Lung Cancer, 2005. 50(3): p. 319-328.
23. Reches, M. and E. Gazit, *Self-assembly of peptide nanotubes and amyloid-like structures by charged-termini-capped diphenylalanine peptide analogues*. Isr J Chem, 2005. 45(3): p. 363-71.

24. Levin, A., et al., *Ostwald's rule of stages governs structural transitions and morphology of dipeptide supramolecular polymers.* Nat Commun, 2014. 5: p. 5219-5226.
25. Roth, J., *The silver anniversary of gold: 25 years of the colloidal gold marker system for immunocytochemistry and histochemistry.* Histochemistry and Cell Biology, 1996. 106(1): p. 1-8.
26. Sau, T. and D. Goia, *Biomedical Applications of Gold Nanoparticles*, in *Fine Particles in Medicine and Pharmacy*, E. Matijević, Editor. 2012, Springer US. p. 101-145.
27. Gazal, S., et al., *Synthesis of novel protected N-alpha (omega-thioalkyl) amino acid building units and their incorporation in backbone cyclic disulfide and thioetheric bridged peptides.* J Pept Res, 2001. 58(6): p. 527-39.
28. Gilon, C., et al., *A backbone-cylic, receptor 5-selective somatostatin analogue: Synthesis, bioactivity, and nuclear magnetic resonance conformational analysis.* J Med Chem, 1998. 41(6): p. 919-29.
29. Falb, E., et al., *A bicyclic and hsst2 selective somatostatin analogue: design, synthesis, conformational analysis and binding.* Bioorg Med Chem, 2001. 9(12): p. 3255-3264.

What is claimed is:

1. A nanoparticle, formed by supramolecular co-assembly of:
    (a) a self-assembled conjugate of a diphenylalanine (FF) dipeptide or analog thereof, covalently bound, directly or through a linker, to a cancer targeting peptide, wherein the cancer targeting peptide is somatostatin or a somatostatin analog; and
    (b) a diphenylalanine (FF) dipeptide or analog thereof, wherein the ratio between the conjugate and the diphenylalanine (FF) dipeptide or analog thereof is about 1:4 to about 1:10.

2. The nanoparticle according to claim 1, wherein the diphenylalanine (FF) dipeptide or analog thereof in the self-assembled conjugate is diphenylalanine (FF) or a protected diphenylalanine (FF), wherein the protected diphenylalanine is an amino-protected diphenylalanine (FF) selected from the group consisting of 9-fluorenylmethoxycarbonyl diphenylalanine (Fmoc-FF), tbutoxycarbonyl-diphenylalanine (Boc-FF), benzyloxycarbonyl (Cbz) diphenylalanine (Cbz-FF), acyl-diphenylalanine (Ac-FF), and silyl phenylalanine (silyl-FF).

3. The nanoparticle according to claim 1, wherein the diphenylalanine (FF) dipeptide or analog thereof in the self-assembled conjugate is conjugated to somatostatin or a somatostatin analog through a linker selected from the group consisting of: a linear or branched C1-C20 alkylene, C2-C20 alkenylene, C2-C20 alkynylene and arylene moiety, each of which optionally incorporates one or more heteroatoms selected from O, N and S in the chain, and which is optionally substituted at either or both ends with a group selected from the group consisting of —NH—, —C(=O)—, —O—, —S—, —C(=O)—O—, —O—C(=O)—O—, —C(=O)—NH—, —NH—C(=O)—NH—, NH—C(=O)—O—, —S(=O)—, —S(=O)—O—, —PO(=O)—O—, and any combination thereof.

4. The nanoparticle according to claim 3, wherein the linker is derived from polyethylene glycol (PEG).

5. The nanoparticle according to claim 4, wherein the linker is represented by the structure:

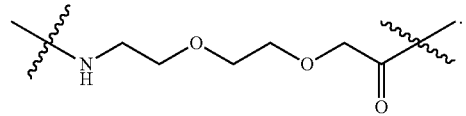 [SMILES: *NCCOCCOCC(*)=O]

6. The nanoparticle according to claim 1, which encapsulates one or more imaging agents.

7. The nanoparticle according to claim 1, having a diameter between about 50 nm and about 250 nm.

8. The nanoparticle according to claim 1, wherein the diphenylalanine (FF) dipeptide or analog thereof in (b) is co-assembled with the conjugate through non-covalent interactions.

9. The nanoparticle according to claim 1, wherein the ratio between the conjugate and the diphenylalanine (FF) dipeptide or analog thereof is about 1:4.

10. The nanoparticle according to claim 1, wherein the diphenylalanine (FF) or analog thereof in (b) is diphenylalanine (FF) or a protected diphenylalanine (FF) selected from the group consisting of an amino-protected diphenylalanine (FF), a carboxy-protected diphenylalanine (FF), an amino-protected, carboxy-protected diphenylalanine (FF), and combinations thereof, wherein the amino-protected diphenylalanine is selected from the group consisting of t-butoxycarbonyl-diphenylalanine (Boc-FF), 9-fluorenylmethoxycarbonyl diphenylalanine (Fmoc-FF), benzyloxycarbonyl (Cbz) diphenylalanine (Cbz-FF), acyl-diphenylalanine (Ac-FF), and silyl phenylalanine (silyl-FF).

11. A pharmaceutical composition comprising the nanoparticle according to claim 1, and a pharmaceutically acceptable carrier.

12. A method for targeting the delivery of an anti-cancer drug, a hormone or a hormone analog to a target tumor, comprising administering the nanoparticle of claim 1.

13. The nanoparticle according to claim 1, which is represented by the structure:
    Fmoc-FF-(PEG)$_2$-PTR:Boc-FF (1:4)
wherein PTR is somatostatin or analog thereof, Fmoc-FF is 9-fluorenylmethoxycarbonyl diphenylalanine, Boc-FF is t-butoxycarbonyl diphenylalanine, and (PEG)$_2$ is a linker derived from polyethylene glycol having the structure

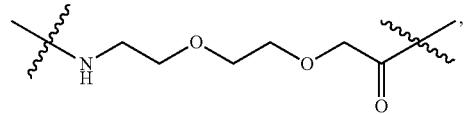 [SMILES: *NCCOCCOCC(*)=O]

and wherein Fmoc-FF-(PEG)$_2$-PTR is represented by the structures as depicted in FIG. 1b.

14. A method of preparing the nanoparticle of claim 1, the method comprising the steps of:
    (a) covalently conjugating somatostatin or a somatostatin analog, directly or through a linker, to diphenylalanine (FF) dipeptide or analog thereof, under conditions sufficient to form a self-assembled conjugate; and
    (b) contacting the product of step (a) with diphenylalanine (FF) dipeptide or analog thereof, under conditions sufficient to form a supramolecular structure, wherein the diphenylalanine (FF) or analog thereof is co-assembled with the conjugate of step (a) through non-covalent interactions and wherein the ratio between the conjugate and the diphenylalanine (FF) dipeptide or analog thereof is about 1:4 to about 1:10.

15. A nanoparticle comprising a self-assembled conjugate of a diphenylalanine (FF) dipeptide or analog thereof, covalently bound, through a linker, to a cancer targeting peptide, wherein the cancer targeting peptide is somatostatin or a somatostatin analog and wherein the linker is selected from the group consisting of: a linear or branched C1-C20 alkylene, C2-C20 alkenylene, C2-C20 alkynylene and arylene moiety, each of which optionally incorporates one or more heteroatoms selected from O, N and S in the chain, and which is optionally substituted at either or both ends with a group selected from the group consisting of —NH—, —C(=O)—, —O—, —S—, —C(=O)—O—, —O—C(=O)—O—, —C(=O)—NH—, —NH—C(=O)—NH—, NH—C(=O)—O—, —S(=O)—, —S(=O)—O—, —PO(=O)—O—, and any combination thereof.

16. The nanoparticle according to claim 15, wherein the diphenylalanine (FF) dipeptide or analog thereof is diphenylalanine (FF) or an amino-protected diphenylalanine (FF) selected from the group consisting of 9-fluorenylmethoxycarbonyl diphenylalanine (Fmoc-FF), t-butoxycarbonyl-diphenylalanine (Boc-FF), benzyloxycarbonyl (Cbz) diphenylalanine (Cbz-FF), acyl-diphenylalanine (Ac-FF), and silyl phenylalanine (silyl-FF).

17. The nanoparticle according to claim 15, wherein the linker is derived from polyethylene glycol (PEG).

18. The nanoparticle according to claim 17, wherein the linker is represented by the structure:

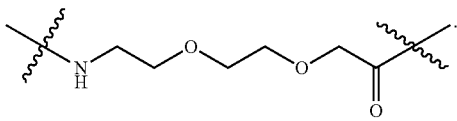 [SMILES: *NCCOCCOCC(*)=O]

19. The nanoparticle according to claim 15, which encapsulates one or more imaging agents.

20. The nanoparticle according to claim 15, which is represented by the structure:
FF-(PEG)$_2$-PTR
wherein PTR is somatostatin or analog thereof, FF is diphenylalanine or analog thereof, and (PEG)$_2$ is a linker represented by the structure

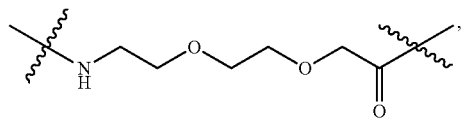

wherein the nanoparticle is represented by the structure depicted in FIG. 1a.

21. The nanoparticle according to claim 15, which is represented by the structure:
Fmoc-FF-(PEG)$_2$-PTR
wherein PTR is somatostatin or analog thereof, Fmoc-FF is 9-fluorenylmethoxycarbonyl diphenylalanine, and (PEG)$_2$ is a linker represented by the structure

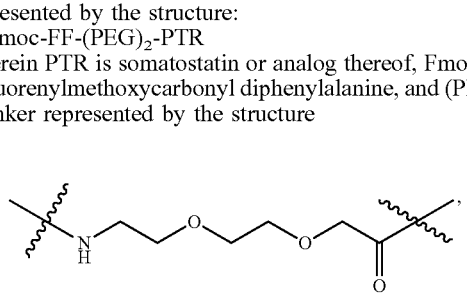

wherein the nanoparticle is represented by the structure depicted in FIG. 1b.

22. The nanoparticle according to claim 1, wherein the somatostatin analog is PTR 3207 or a derivative thereof.

23. The nanoparticle according to claim 15, wherein the somatostatin analog is PTR 3207 or a derivative thereof.

24. A method for imaging a tumor, comprising administering by injection the nanoparticle of claim 6.

* * * * *